(12) United States Patent
Tsukamoto et al.

(10) Patent No.: US 12,415,088 B2
(45) Date of Patent: Sep. 16, 2025

(54) LIGHT IRRADIATION DEVICE AND LIGHT IRRADIATION SYSTEM

(71) Applicant: ASAHI INTECC CO., LTD., Seto (JP)

(72) Inventors: Toshihiko Tsukamoto, Seto (JP); Yuko Katsurada, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 849 days.

(21) Appl. No.: 17/701,225

(22) Filed: Mar. 22, 2022

(65) Prior Publication Data

US 2022/0212024 A1 Jul. 7, 2022

Related U.S. Application Data

(63) Continuation of application No. PCT/JP2020/030984, filed on Aug. 17, 2020.

(30) Foreign Application Priority Data

Sep. 24, 2019 (JP) .................................. 2019-172566

(51) Int. Cl.
*A61N 5/06* (2006.01)
*F21V 8/00* (2006.01)

(52) U.S. Cl.
CPC ........... *A61N 5/0601* (2013.01); *A61N 5/062* (2013.01); *A61N 2005/0643* (2013.01); *A61N 2005/0659* (2013.01); *A61N 2005/0664* (2013.01); *G02B 6/0008* (2013.01)

(58) Field of Classification Search
CPC .................. A61N 5/0601; A61N 5/062; A61N 2005/0643; A61N 2005/0659; A61N 2005/0664; A61N 2005/063; A61N 2005/0632; A61N 5/0613; G02B 6/0008; A61B 18/20–18/28

See application file for complete search history.

(56) References Cited

U.S. PATENT DOCUMENTS

| 4,989,931 A | 2/1991 | Mori | |
| 11,109,912 B2* | 9/2021 | Brown | ................ A61B 18/245 |
| 2003/0060867 A1 | 3/2003 | Weber | |

(Continued)

FOREIGN PATENT DOCUMENTS

| JP | S62161381 A | 7/1987 |
| JP | 2003265631 A | 9/2003 |

(Continued)

OTHER PUBLICATIONS

Makoto Mitsunaga, et al., "Cancer Cell-Selective In Vivo Near Infrared Photoimmunotherapy Targeting Specific Membrane Molecules", Nature Medicine vol. 17, No. 12, pp. 1685-1691, Jun. 1, 2012.

(Continued)

*Primary Examiner* — Jonathan T Kuo
(74) *Attorney, Agent, or Firm* — Oliff PLC

(57) ABSTRACT

A light irradiation device having an elongated shape is inserted into a catheter. The light irradiation device includes a light irradiation portion provided on a distal end side of a light irradiation device for outputting irradiation light to outside, and a large diameter portion positioned distal to the light irradiation portion and having an outer diameter larger than an outer diameter of the light irradiation portion.

20 Claims, 17 Drawing Sheets

(56) References Cited

U.S. PATENT DOCUMENTS

| | | | |
|---|---|---|---|
| 2003/0171741 A1* | 9/2003 | Ziebol | A61B 18/245 606/7 |
| 2013/0051728 A1 | 2/2013 | Petroff et al. | |
| 2016/0278862 A1* | 9/2016 | Ko | A61B 18/24 |
| 2018/0008122 A1 | 1/2018 | Arai et al. | |
| 2018/0303548 A1* | 10/2018 | Brown | A61B 18/245 |

FOREIGN PATENT DOCUMENTS

| | | |
|---|---|---|
| JP | 2005534409 A | 11/2005 |
| JP | 2005538751 A | 12/2005 |
| JP | 2007528752 A | 10/2007 |
| JP | 2010529885 A | 9/2010 |
| JP | 2014523907 A | 9/2014 |
| JP | 2018000867 A | 1/2018 |
| WO | 03077723 A2 | 9/2003 |
| WO | 2004012805 A2 | 2/2004 |
| WO | 2005007216 A2 | 1/2005 |
| WO | 2008156623 A1 | 12/2008 |
| WO | 2013009475 A1 | 1/2013 |
| WO | 2020/023778 A1 | 1/2020 |

OTHER PUBLICATIONS

Kazuhide Sato, et al., "Spatially selective depletion of tumor-associated regulatory T cells with near-infrared photoimmunotherapy", Science Translational Medicine, vol. 8, Issue 352 ra110, Aug. 17, 2016.

Shuhei Okuyama, et al., "Interstitial near-infrared photoimmunotherapy: effective treatment areas and light doses needed for use with fiber optic diffusers", Oncotarget; vol. 9, No. 13, pp. 11159-11169, Jan. 27, 2018.

* cited by examiner

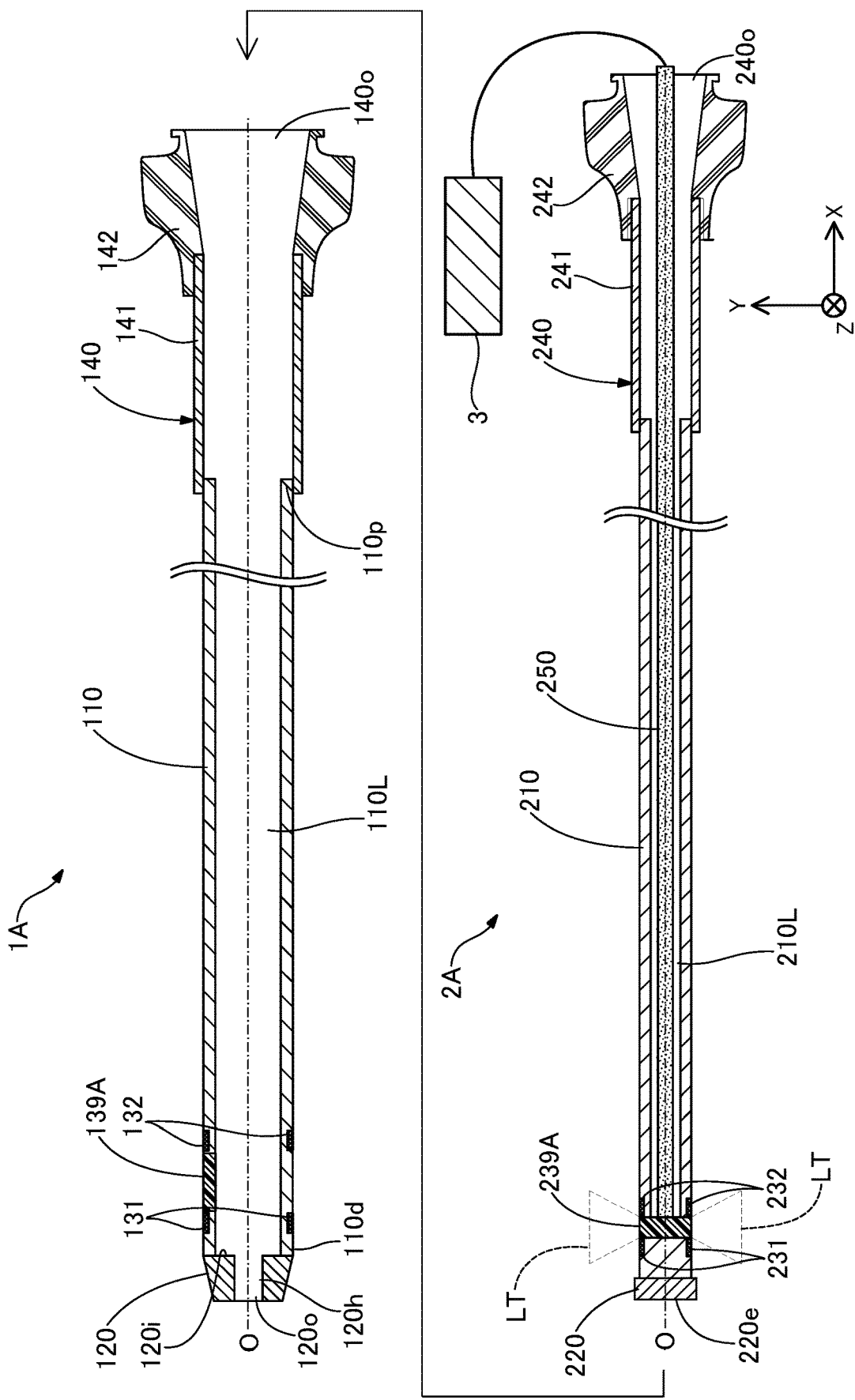

Fig. 9

| No. | TARGET | EXAMPLE | TARGET | EXAMPLE |
|---|---|---|---|---|
| 1 | ENTIRE CIRCUMFERENCE | LIGHT TRANSMITTING PORTION 139 | PARTIAL CIRCUMFERENCE | LIGHT IRRADIATION PORTION 239 |
| 2 | PARTIAL CIRCUMFERENCE | LIGHT TRANSMITTING PORTION 139A | ENTIRE CIRCUMFERENCE | LIGHT IRRADIATION PORTION 239A |
| 3 | ENTIRE CIRCUMFERENCE | LIGHT TRANSMITTING PORTION 139 | ENTIRE CIRCUMFERENCE | LIGHT IRRADIATION PORTION 239A |
| 4 | PARTIAL CIRCUMFERENCE | LIGHT TRANSMITTING PORTION 139A | PARTIAL CIRCUMFERENCE | LIGHT IRRADIATION PORTION 239 |

LIGHT IRRADIATION DEVICE AND LIGHT IRRADIATION SYSTEM

CROSS REFERENCE TO RELATED APPLICATIONS

The present application is a Bypass Continuation of PCT/JP2020/030984 filed Aug. 17, 2020, which is based upon and claims priority from JP 2019-172566 filed on Sep. 24, 2019, the entirety of the prior applications being hereby incorporated by reference into this application.

TECHNICAL FIELD

The disclosed embodiments relate to a light irradiation device and a light irradiation system.

BACKGROUND ART

In cancer treatment, surgical, radiological, and pharmacological (chemical) methods are used alone or in combination, and development of each of these techniques is progressing in recent years. However, there are many cancers for which a satisfactory treatment technique has not yet been found, and further development of the treatment techniques is expected. A method called photodynamic therapy (PDT) is known as one of these cancer treatment techniques. In the PDT, a photosensitizer is administered intravenously and then irradiated with light, to generate reactive oxygen in cancer cells and kill the cancer cells (see, for example, Non-Patent Literature 1). However, in the PDT, the photosensitizer is accumulated with low selectivity in the cancer cells, so that the magnitude of the side effects caused by the uptake of the photosensitizer into normal cells is an issue, and thus, the PDT is not widely used as a treatment technique.

Therefore, a treatment technique attracting attention in recent years is near-infrared photoimmunotherapy (NIR-PIT). The NIR-PIT uses a conjugate in which two compounds, an antibody against a specific antigen of cancer cells and a photosensitizer (for example, IRDye 700DX), are bound. When administered intravenously, this conjugate selectively accumulates in cancer cells in the body. Subsequently, if the conjugate is irradiated with light having an excitation wavelength (for example, 690 nm) of the photosensitizer in the conjugate, the conjugate is activated and exhibits an anticancer effect (see, for example, Patent Literature 1). Selective accumulation of the antibody in the cancer and local light irradiation in the NIR-PIT allow for reduction of side effects compared to the PDT. Further, in the NIR-PIT, irradiation with light in the near-infrared region of 690 nm (NIR irradiation) is performed, for example, and thus, an effect of the NIR irradiation on the immune system can also be expected (see, for example, Non-Patent Literature 2).

A predetermined wavelength region including the 690 nm region in the example described above is also called a spectroscopic window of a living body. Although light in this wavelength region is absorbed less by biological components than light in other wavelength regions, the light does not sufficiently penetrate when light irradiation is performed from the body surface, and thus, there is a problem in that the NIR-PIT cannot be applied to cancers in a deep part inside the body. Therefore, in recent years, research is being conducted on the NIR-PIT in which light irradiation is performed at a position closer to cancer cells, instead of light irradiation from the body surface (see, for example, Non-Patent Literature 3). For example, Patent Literatures 2 to 5 disclose devices usable in such PDT and NIR-PIT. All of the devices described in Patent Literatures 2 to 5 are inserted into a blood vessel for use and can be used to perform light irradiation in a deep part inside the body.

CITATION LIST

Patent Literature

Patent Literature 1: JP 2014-523907 W
Patent Literature 2: JP 2018-000867 A
Patent Literature 3: JP 2007-528752 W
Patent Literature 4: JP 2005-534409 W
Patent Literature 5: JP 2003-265631 A

Non-Patent Literature

Non-Patent Literature 1: Makoto Mitsunaga, Mikako Ogawa, Nobuyuki Kosaka Lauren T. Rosenblum, Peter L. Choyke, and Hisataka Kobayashi, Cancer Cell-Selective In Vivo Near Infrared Photoimmunotherapy Targeting Specific Membrane Molecules, Nature Medicine 2012 17(12): p. 1685-1691

Non-Patent Literature 2: Kazuhide Sato, Noriko Sato, Biying Xu, Yuko Nakamura, Tadanobu Nagaya, Peter L. Choyke, Yoshinori Hasegawa, and Hisataka Kobayashi, Spatially selective depletion of tumor-associated regulatory T cells with near-infrared photoimmunotherapy, Science Translational Medicine 2016 Vol. 8 Issue 352, ra110

Non-Patent Literature 3: Shuhei Okuyama, Tadanobu Nagaya, Kazuhide Sato, Fusa Ogata, Yasuhiro Maruoka, Peter L. Choyke, and Hisataka Kobayashi, Interstitial near-infrared photoimmunotherapy: effective treatment areas and light doses needed for use with fiber optic diffusers, Oncotarget 2018 Feb. 16; 9(13): p. 11159-11169

SUMMARY

Technical Problem

Here, in the PDT and the NIR-PIT, as described above, the cancer cells having the accumulated conjugate are irradiated with light of the excitation wavelength of the photosensitizer in the conjugate to kill the cancer cells. However, it is preferable to avoid irradiation to normal cells other than the cancer cells with light because this leads to blood coagulation and damage of normal cells.

Further, in the PDT and the NIR-PIT, a light irradiation system separately provided with a catheter including a light transmitting portion transmitting light and a light irradiation device (a probe body) including a light irradiation portion outputting irradiation light may be used. In such a light irradiation system, the catheter usually has a tube shape for inserting a guide wire or a light irradiation device into the catheter. Therefore, when the catheter is inserted into a blood vessel ahead of the light irradiation device, blood infiltrates the inside of the catheter. In such a state, when the light irradiation device is inserted into the inside of the catheter to perform light irradiation, blood infiltrating the inside of the catheter is also inadvertently irradiated with light, which is not favorable. In this regard, in the devices described in Patent Literatures 2 to 5, in a technique in which a catheter and a light irradiation device are used in combination, no consideration is given to suppressing light irradiation to blood in the catheter.

It is noted that such a problem is not limited to the PDT and the NIR-PIT, and is common to all devices used in examinations or treatments including a light irradiation process in the body. Further, such a problem is not limited to devices inserted into a blood vessel, and is common to all devices inserted into living body lumens, such as the vascular system, the lymphatic system, the biliary system, the urinary system, the respiratory system, the digestive system, secretory glands, and reproductive organs.

The disclosed embodiments have been contrived to solve at least a part of the above-mentioned problems, and an object of the disclosed embodiments is to suppress, in a technique in which a catheter and a light irradiation device are used in combination, light irradiation to body fluid in the catheter.

Solution to Problem

The disclosed embodiments have been contrived to solve at least a part of the above-described problems, and can be implemented as the following aspects.

(1) According to one aspect of the disclosed embodiments, a light irradiation device having an elongated shape and being inserted into a catheter for use is provided. The light irradiation device includes a light irradiation portion being provided on a distal end side of the light irradiation device and outputting irradiation light to an outside, and a large diameter portion being distal to the light irradiation portion and having an outer diameter larger than an outer diameter of the light irradiation portion.

According to this configuration, the light irradiation device inserted into the catheter for use includes the large diameter portion having an outer diameter larger than the outer diameter of the light irradiation portion. Therefore, when the light irradiation device is inserted into the catheter, body fluid infiltrating an inside of the catheter can be pushed out to the distal end side beyond the light irradiation portion by the large diameter portion distal to the light irradiation portion, and thus, the body fluid can be removed from a vicinity of the light irradiation portion. As a result, according to the light irradiation device of the present configuration, it is possible to suppress light irradiation of the body fluid in the catheter, and thus, the light irradiation device can contribute to the suppression of coagulation of the body fluid due to light irradiation and the suppression of damage to living tissue.

(2) In the light irradiation device in the aspect described above, the large diameter portion may have a substantially columnar shape extending in a longitudinal direction of the light irradiation device, and a groove portion extending in the longitudinal direction may be formed on an outer peripheral surface of the large diameter portion. According to this configuration, the groove portion extending in the longitudinal direction is formed on the outer peripheral surface of the large diameter portion, and thus, if the groove portion is caused to function as an air discharge hole, the light irradiation device can be smoothly slid (moved in the longitudinal direction) in the catheter.

(3) According to one aspect of the disclosed embodiments, a light irradiation system is provided. The light irradiation system includes the light irradiation device in the aspect described above and a catheter having an elongated tube shape into which the light irradiation device is inserted, the catheter may include a light transmitting portion being provided on a distal end side of the catheter and transmitting light inside a tube to the outside, and an inner diameter of the catheter may be equal to or larger than the outer diameter of the large diameter portion of the light irradiation device.

According to this configuration, it is possible to provide a light irradiation system in which the catheter including the light transmitting portion and the light irradiation device including the light irradiation portion are separately provided, and thus, the degree of freedom in designing the device can be improved and the range of procedures can be expanded. Further, the inner diameter of the catheter is equal to or larger than the outer diameter of the large diameter portion of the light irradiation device, so that the light irradiation device can be smoothly slid in the catheter.

(4) In the light irradiation system in the aspect described above, the catheter may further include a through-hole being distal to the light transmitting portion and communicating the inside and outside of the tube.

According to this configuration, the catheter is provided with the through-hole communicating the inside and outside of the tube, and thus, body fluid inside the catheter that is pushed out by the large diameter portion of the light irradiation device can be ejected to the outside of the catheter from the through-hole.

(5) In the light irradiation system in the aspect described above, the through-hole of the catheter may communicate between the inside and outside of the tube in a longitudinal direction of the catheter, and an opening diameter of the through-hole may be smaller than the outer diameter of the large diameter portion of the light irradiation device.

According to this configuration, the through-hole of the catheter communicates between the inside and outside of the tube in the longitudinal direction of the catheter, and thus, the through-hole can also be used as an insertion port of a guide wire lumen for inserting a guide wire into the catheter.

(6) In the light irradiation system in the aspect described above, a protruding portion to be engaged with the through-hole of the catheter may be formed on a distal end side of the large diameter portion of the light irradiation device.

According to this configuration, when the light irradiation device is inserted into the catheter, the protruding portion formed on the distal end side of the large diameter portion of the light irradiation device is engaged with the through-hole of the catheter, so that the light irradiation device and the catheter can be easily positioned in the long axis direction.

(7) In the light irradiation system in the aspect described above, in a state where the light irradiation device is inserted into the catheter and the protruding portion is engaged with the through-hole, a length between an outer peripheral surface of the protruding portion and an inner peripheral surface of the through-hole may be shorter than a length between the outer peripheral surface of the large diameter portion and an inner peripheral surface of the catheter.

According to this configuration, the slidability of the light irradiation device in the catheter can be improved, and the light irradiation device and the catheter can be surely positioned in the long axis direction.

It is noted that the disclosed embodiments can be realized in various aspects, for example, the disclosed embodiments can be realized in aspects such as a catheter, a light irradiation device, a light irradiation system provided with the catheter and the light irradiation device separately or integrally, and a manufacturing method of the catheter, the light irradiation device, and the light irradiation system.

BRIEF DESCRIPTION OF DRAWINGS

FIG. 8 is an explanatory diagram illustrating a configuration of a light irradiation system according to a second embodiment.

FIG. 9 is an explanatory table showing combinations of a light transmitting portion and a light irradiation portion.

DETAILED DESCRIPTION OF EMBODIMENTS

First Embodiment

Figure 1:
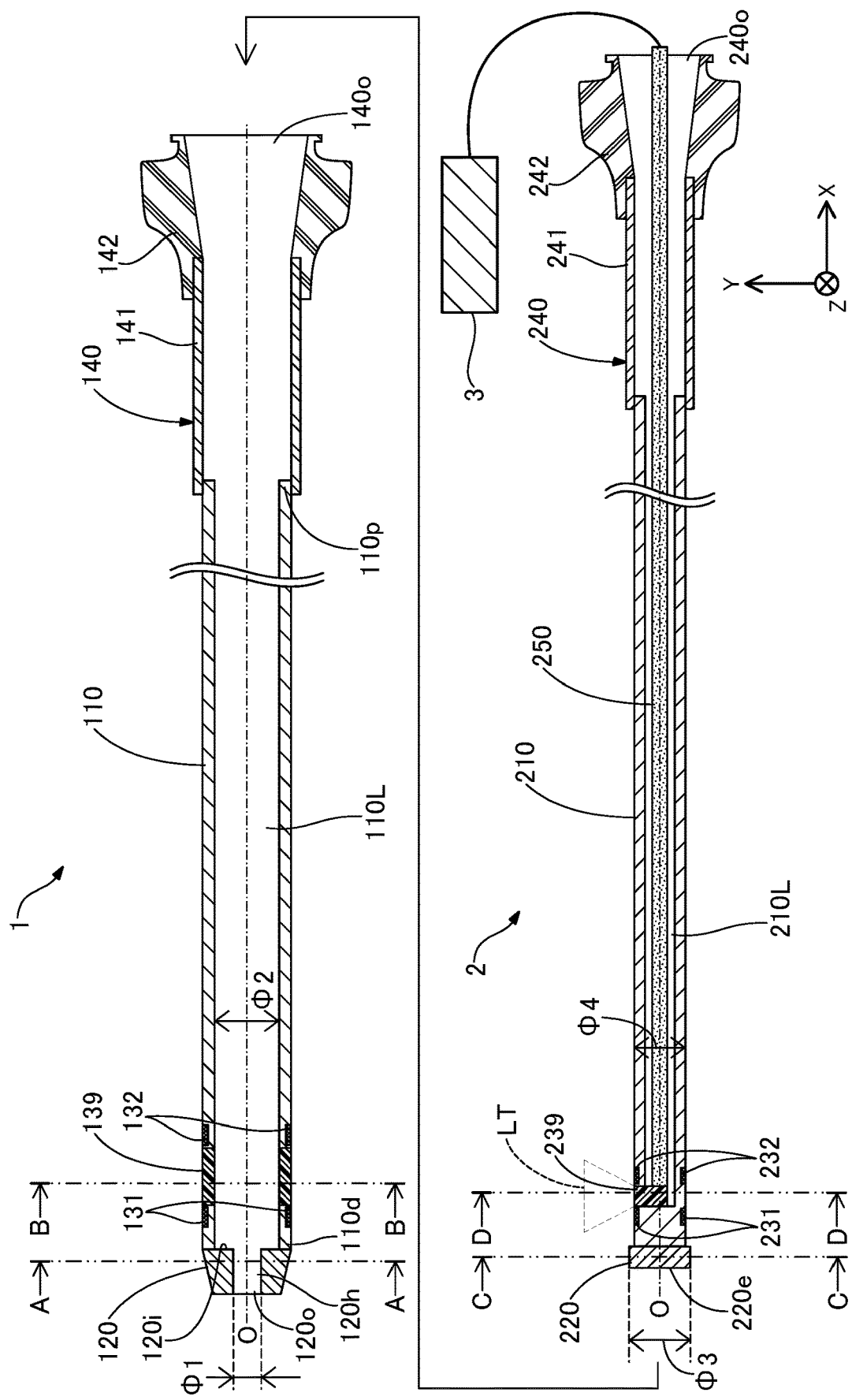
FIG. 1 is an explanatory diagram illustrating a configuration of a light irradiation system according to a first embodiment.

FIG. 1 is an explanatory diagram illustrating a configuration of a light irradiation system according to a first embodiment. The light irradiation system is a system for irradiating living tissue with light, from inside the living body lumen by being inserted for use into a living body lumen such as the vascular system, the lymphatic system, the biliary system, the urinary system, the respiratory system, the digestive system, secretory glands, and reproductive organs. The light irradiation system can be used in photodynamic therapy (PDT) and near-infrared photoimmunotherapy (NIR-PIT), for example. In the following embodiments, laser light is described as an example of light, but the light being used is not limited to the laser light and the light irradiation system may have a configuration employing LED light or white light, for example. The light irradiation system includes a catheter 1 and a light irradiation device 2 to be inserted into the catheter 1 for use. In FIG. 1, the catheter 1 and the light irradiation device 2 are illustrated separately.

In FIG. 1, an axis passing through a center of the catheter 1 and an axis passing through a center of the light irradiation device 2 are represented by an axis O (dash-dot-dash line). Hereinafter, in a state where the light irradiation device 2 is inserted into the catheter 1, it is assumed that axes passing through the centers of the light irradiation device 2 and the catheter 1 coincide with the axis O, but the axes passing through the centers of the light irradiation device 2 and the catheter 1 when the light irradiation device 2 is inserted into the catheter 1 may be different from each other. Further, in FIG. 1, an X-axis, a Y-axis, and a Z-axis that are orthogonal to each other are illustrated. The X-axis corresponds to a longitudinal direction of the catheter 1 and the light irradiation device 2 (a direction of the axis O), the Y-axis corresponds to a height direction of the catheter 1 and the light irradiation device 2, and the Z-axis corresponds to a width direction of the catheter 1 and the light irradiation device 2. The left side (a −X-axis direction) in FIG. 1 is referred to as a "distal end side" of the catheter 1, the light irradiation device 2, and each constitution component, and the right side (a +X-axis direction) in FIG. 1 is referred to as a "proximal end side" of the catheter 1, the light irradiation device 2, and each constitution component. Further, end portions of the catheter 1, the light irradiation device 2, and each constitution component located on the distal end side are referred to as a "distal end", and the distal end and a vicinity thereof are referred to as a "distal end portion". Moreover, end portions of the catheter 1, the light irradiation device 2, and each constitution component located on the proximal end side are referred to as a "proximal end", and the proximal end and a vicinity thereof are referred to as a "proximal end portion". The distal end side corresponds to a "distal side" inserted into a living body, and the proximal end side corresponds to a "proximal side" operated by an operator such as a doctor. These features are common to each drawing in FIG. 1 and following illustrating an overall configuration.

The catheter 1 has an elongated tube shape and includes a shaft 110, a distal tip 120, and a connector 140. The shaft 110 is an elongated member extending along the axis O. The shaft 110 has a substantially hollow cylindrical shape (a tube shape) and both ends of the shaft 110, i.e., a distal end portion 110d and a proximal end portion 110p, are open. The shaft 110 includes a lumen 110L inside the shaft 110. The lumen 110L functions as a guide wire lumen for inserting a guide wire through the catheter 1 during delivery of the catheter 1. The lumen 110L functions as a device lumen for inserting the light irradiation device 2 into the catheter 1 after the delivery of the catheter 1. Using a single lumen serving as both the guide wire lumen and the device lumen, as described above, makes it possible to reduce the diameter of the catheter 1. The shaft 110 may have any outer diameter, inner diameter, and length.

Figure 2:
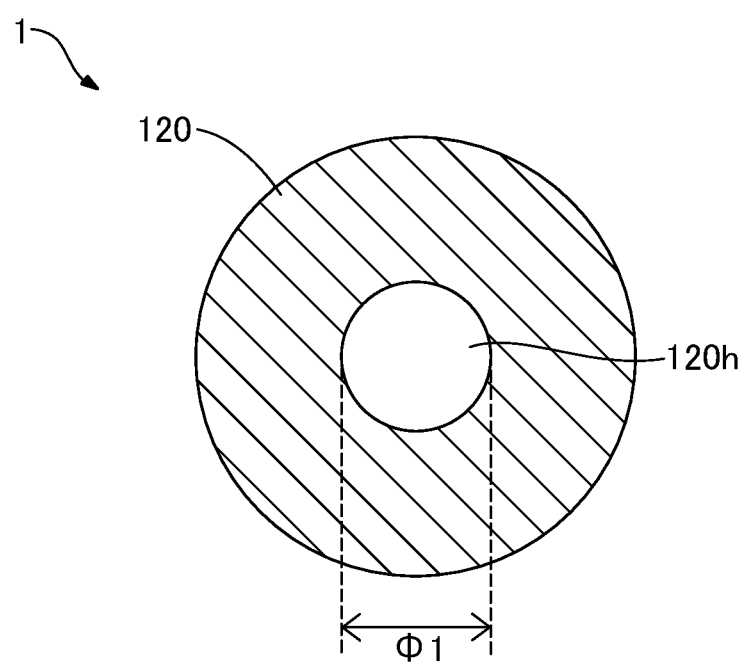
FIG. 2 is an explanatory diagram illustrating a cross-sectional configuration taken along line A-A of FIG. 1.

FIG. 2 is an explanatory diagram illustrating a cross-sectional configuration taken along line A-A of FIG. 1. The distal tip 120 is a member that is joined to the distal end portion of the shaft 110 and advances in a living body lumen ahead of other members. As illustrated in FIG. 1, to facilitate progress of the catheter 1 in the living body lumen, the distal tip 120 has an outer shape with a diameter decreasing from the proximal end side to the distal end side. Further, as illustrated in FIG. 2, a through-hole 120h penetrating the distal tip 120 in the direction of the axis O is formed in a substantially central part of the distal tip 120. In other words, the through-hole 120h communicates between the inside and outside of the shaft 110 in the longitudinal direction (the direction of the axis O) of the catheter 1. Here, an opening diameter phi 1 of the through-hole 120h is smaller than an inner diameter phi 2 of the lumen 110L of the shaft 110. Therefore, as illustrated in FIG. 1, at a boundary between the shaft 110 and the distal tip 120, an inner surface 120i of the distal tip 120 protrudes to form a step. An opening 120o of the distal tip 120 leads to the through-hole 120h and is used when inserting a guide wire (not illustrated) into the catheter 1. The distal tip 120 may have any outer diameter and length.

The connector 140 is a member arranged on the proximal end side of the catheter 1 and gripped by the operator. The connector 140 includes a connection portion 141 having a substantially hollow cylindrical shape and a pair of blades 142. A distal end portion of the connection portion 141 is joined to the proximal end portion 110p of the shaft 110, and a proximal end portion of the connection portion 141 is joined with the blades 142. The blades 142 and the connector 140 may be integrated. An opening 140o of the connector 140 leads to the lumen 110L via the inside of the connector 140, and is used when inserting the light irradiation device 2 into the catheter 1. The connection portion 141 may have any outer diameter, inner diameter, and length, and the blades 142 may have any shape.

Figure 3:
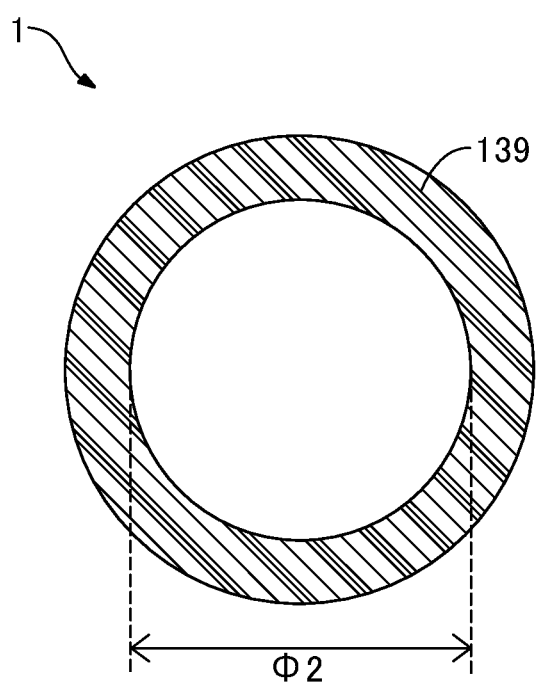
FIG. 3 is an explanatory diagram illustrating a cross-sectional configuration taken along line B-B of FIG. 1.

FIG. 3 is an explanatory diagram illustrating a cross-sectional configuration taken along line B-B of FIG. 1. The shaft 110 of the catheter 1 is further provided with a light transmitting portion 139 and first marker portions 131 and 132. The light transmitting portion 139 transmits light inside the shaft 110 to the outside. As illustrated in FIGS. 1 and 3, the light transmitting portion 139 is a hollow member having a substantially hollow cylindrical shape, has an outer diameter substantially the same as the outer diameter of the shaft 110, and an inner diameter substantially the same as the inner diameter phi 2 of the lumen 110L of the shaft 110. In other words, the light transmitting portion 139 is provided over the entire circumference, and transmits light inside the shaft 110 to the outside over the entire circumference. The light transmitting portion 139 is joined to the shaft 110 at each of the proximal end side and the distal end side. The light transmitting portion 139 can be formed of a transparent resin material having light-transmitting properties, such as an acrylic resin, polyethylene terephthalate, and polyvinyl chloride.

The first marker portions 131 and 132 function as marks indicating positions of the light transmitting portion 139. The first marker portion 131 is provided close to the distal end portion of the light transmitting portion 139, and functions as a mark indicating a position of the distal end portion of the light transmitting portion 139. The first marker portion 132 is provided close to the proximal end portion of the light transmitting portion 139, and functions as a mark indicating a position of the proximal end portion of the light transmitting portion 139. The first marker portions 131 and 132 are hollow members each having a substantially hollow cylindrical shape. In the example of FIG. 1, the first marker portions 131 and 132 are respectively arranged in recess portions formed on an outer surface of the shaft 110 and are joined to the outer surface of the shaft 110. In other words, the first marker portions 131 and 132 are each embedded in the outer surface of the shaft 110 to surround the shaft 110 in the circumferential direction. It is noted that the first marker portions 131 and 132 may be joined to the outer surface of the shaft 110 without the recess portions, and may protrude from the outer surface of the shaft 110. At least one of the first marker portions 131 and 132 may be omitted.

The light irradiation device 2 has an elongated shape and includes a shaft 210, a distal tip 220, and a connector 240. The shaft 210 is an elongated member extending along the axis O. The shaft 210 has a bottomed cylindrical shape having a closed distal end portion and an open proximal end portion. The shaft 210 includes a lumen 210L inside the shaft 210. An optical fiber 250 is inserted into and fixed to the lumen 210L. A proximal end portion of the optical fiber 250 is directly connected via a connector (not illustrated) or indirectly connected via another optical fiber, to a laser light generator 3 configured to generate laser light of any wavelength. At a distal end portion of the optical fiber 250, a clad and a coating are removed from the optical fiber to expose a core of the optical fiber 250.

Figure 4:
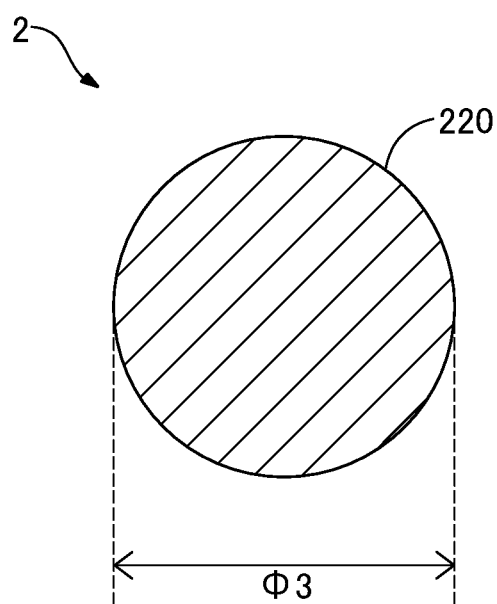
FIG. 4 is an explanatory diagram illustrating a cross-sectional configuration taken along line C-C of FIG. 1.

FIG. 4 is an explanatory diagram illustrating a cross-sectional configuration taken along line C-C of FIG. 1. The distal tip 220 is a member that is joined to the distal end portion of the shaft 210 and advances ahead of other members in the lumen 110L of the catheter 1. As illustrated in FIG. 1, the distal tip 220 is a member having a substantially columnar shape extending in the longitudinal direction of the light irradiation device 2. Here, an outer diameter phi 3 (FIGS. 1 and 4) of the distal tip 220 is larger than an outer diameter phi 4 of the shaft 210 and a light irradiation portion 239 (phi 3>phi 4). Further, it is preferable that the outer diameter phi 3 of the distal tip 220 is larger than the opening diameter phi 1 of the through-hole 120h of the catheter 1 and is equal to or less than the inner diameter phi 2 of the shaft 110 and the light transmitting portion 139 of the catheter 1 (phi 1<phi 3≤phi2). The distal tip 220 functions as a "large diameter portion" that pushes out body fluid infiltrating the lumen 110L of the catheter 1 toward the distal end side from the light irradiation portion 239 when the light irradiation device 2 is inserted into the catheter 1. Details are described later.

The connector 240 is a member arranged on the proximal end side of the light irradiation device 2 and gripped by the operator. The connector 240 includes a connection portion 241 having a substantially hollow cylindrical shape and a pair of blades 242. A distal end portion of the connection portion 241 is joined to a proximal end portion of the shaft 210, and a proximal end portion of the connection portion 241 is joined with the blades 242. The blades 242 and the connector 240 may be integrated.

Figure 5:
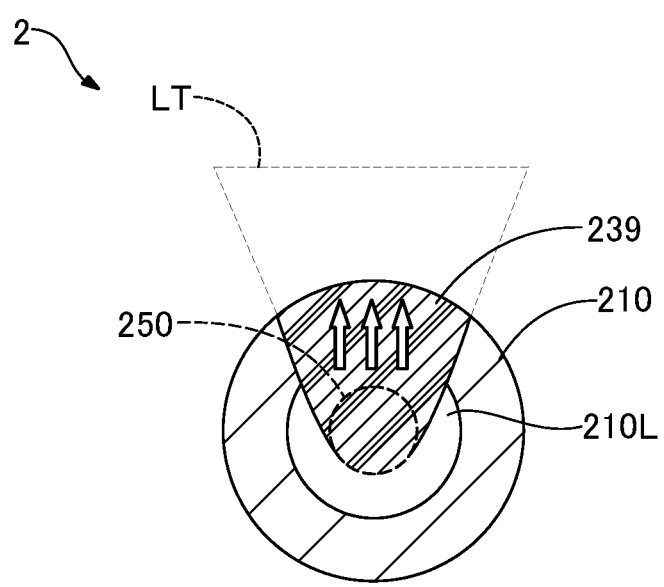
FIG. 5 is an explanatory diagram illustrating a cross-sectional configuration taken along line D-D of FIG. 1.

FIG. 5 is an explanatory diagram illustrating a cross-sectional configuration taken along line D-D of FIG. 1. The shaft 210 of the light irradiation device 2 is further provided with the light irradiation portion 239 and second marker portions 231 and 232. The light irradiation portion 239 outputs, for irradiation, emission light LT from the core exposed at the distal end portion of the optical fiber 250, to the outside in one direction (FIG. 5: white arrows) of a side surface of the light irradiation device 2. As illustrated in FIG. 5, the light irradiation portion 239 is a resin body that covers a distal end of the core of the optical fiber 250 and is provided to be exposed in a part of a side surface of the shaft 210. The light irradiation portion 239 can be formed, for example, by applying fine quartz powder to a dispersed acrylic ultraviolet-curable resin and curing the resultant resin with ultraviolet light. It is noted that the light irradiation portion 239 may be realized in another manner, and may be realized, for example, by a light-reflecting mirror, instead of the resin body. Further, the core exposed at the distal end portion of the optical fiber 250 may be subjected to a well-known process (for example, a process of diagonally cutting a distal end surface, a process of forming a notch, a sandblast process, and a chemical process), to form the light irradiation portion 239 in a part of the optical fiber 250.

Laser light LT generated by the laser light generator 3 is transmitted from the proximal end side to the distal end side of the optical fiber 250 via the core of the optical fiber, and is output, for irradiation, from the core exposed at the distal end portion via the light irradiation portion 239 to the outside, in one direction (FIG. 5: white arrows) of the side surface of the light irradiation device 2.

The second marker portions 231 and 232 function as marks indicating positions of the light irradiation portion 239. The second marker portion 231 is provided close to the distal end portion of the light irradiation portion 239, and functions as a mark indicating a position of the distal end portion of the light irradiation portion 239. The second marker portion 232 is provided close to the proximal end portion of the light irradiation portion 239, and functions as a mark indicating a position of the proximal end portion of the light irradiation portion 239. The second marker portions 231 and 232 are hollow members each having a substantially hollow cylindrical shape. In the example of FIG. 1, the second marker portions 231 and 232 are respectively arranged in recess portions formed on an outer surface of the shaft 210 and are joined to the outer surface of the shaft 210. In other words, the second marker portions 231 and 232 are each embedded in the outer surface of the shaft 210 to surround the shaft 210 in a circumferential direction. It is noted that the second marker portions 231 and 232 may be joined to the outer surface of the shaft 210 without the recess portions, and may protrude from the outer surface of the shaft 210. At least one of the second marker portions 231 and 232 may be omitted.

The first marker portions 131 and 132 of the catheter 1 and the second marker portions 231 and 232 of the light irradiation device 2 may be formed of a radiopaque resin material or a radiopaque metal material. For example, when a resin material is used, the first marker portions 131 and 132 and the second marker portions 231 and 232 may be formed by mixing a radiopaque material such as bismuth trioxide, tungsten, or barium sulfate with a polyamide resin, a polyolefin resin, a polyester resin, a polyurethane resin, a silicon resin, a fluororesin, or the like. For example, when a metal material is used, the first marker portions 131 and 132 and the second marker portions 231 and 232 may be formed of a radiopaque material such as gold, platinum, tungsten, or an alloy containing these elements (for example, a platinum-nickel alloy).

The shaft 110 of the catheter 1 and the shaft 210 of the light irradiation device 2 are preferably antithrombotic, flexible, and biocompatible, and may be formed of a resin material or a metal material. Examples of the resin material may include a polyamide resin, a polyolefin resin, a polyester resin, a polyurethane resin, a silicon resin, and a fluororesin. Examples of the metal material may include stainless steel such as SUS304, a nickel-titanium alloy, a cobalt-chromium alloy, and tungsten steel. Further, the shaft 110 and the shaft 210 can be formed as a bonded structure obtained by combining a plurality of the above-mentioned materials. The distal tip 120 of the catheter 1 and the distal tip 220 of the light irradiation device 2 are preferably flexible, and may be formed of, for example, a resin material such as polyurethane and a polyurethane elastomer. The connector 140 of the catheter 1 and the connector 240 of the light irradiation device 2 may be formed of a resin material such as polyamide, polypropylene, polycarbonate, polyacetal, and polyether sulfone.

Figure 6:
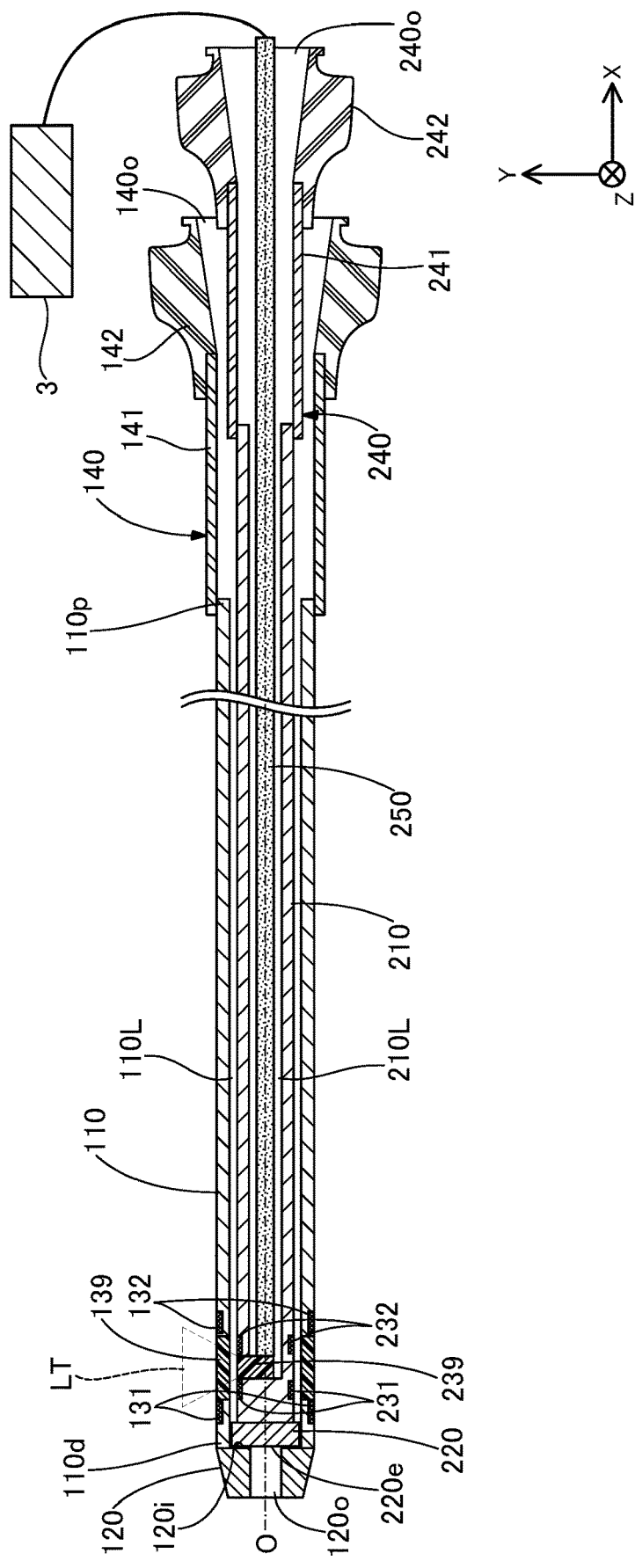
FIG. 6 is an explanatory diagram illustrating a usage state of the light irradiation system.
Figure 7:
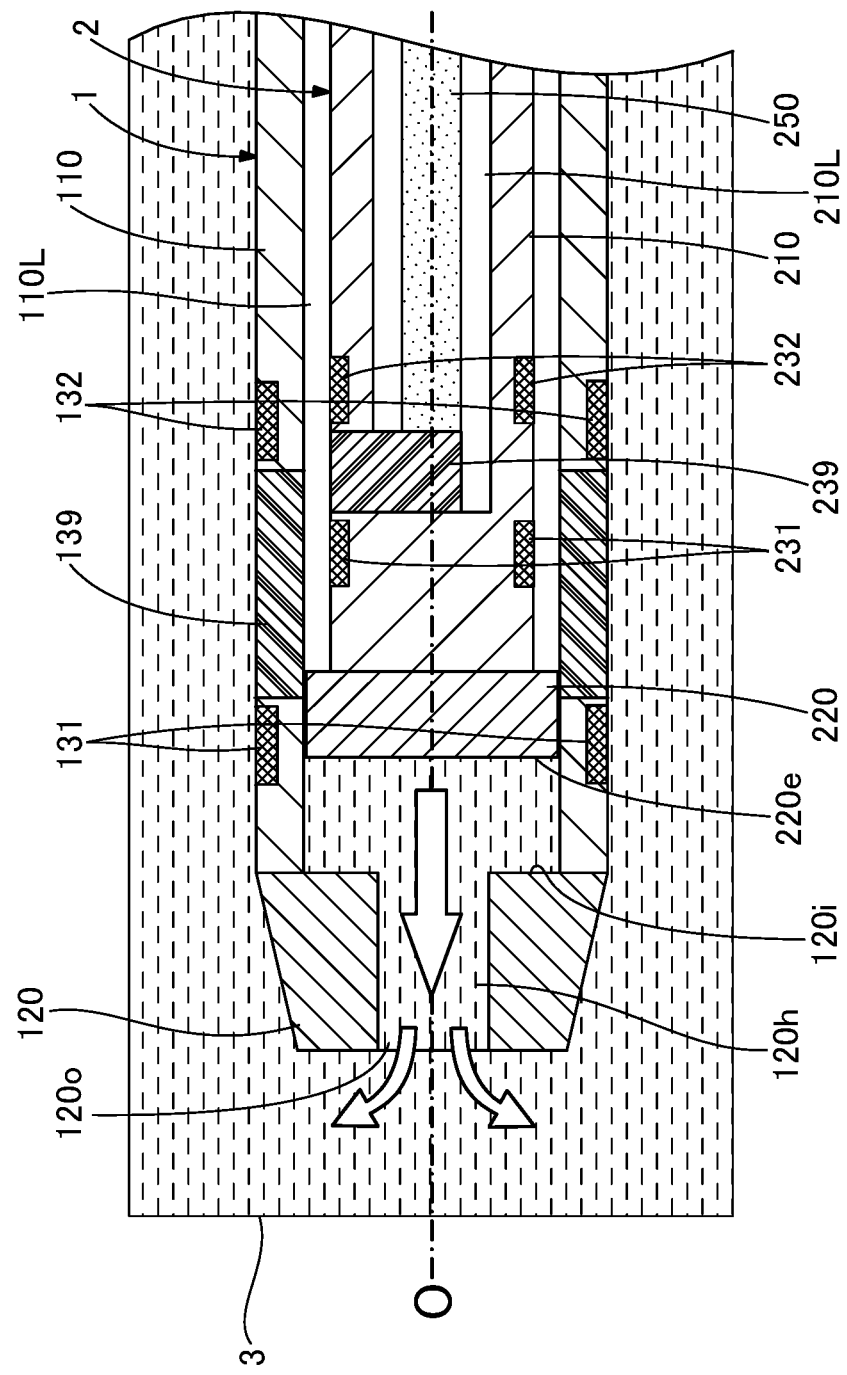
FIG. 7 is an explanatory diagram illustrating a usage state of the light irradiation system.

FIGS. 6 and 7 are explanatory diagrams illustrating a usage state of the light irradiation system. FIG. 6 illustrates an overall view when the light irradiation device 2 is inserted into the catheter 1, and FIG. 7 illustrates an enlarged view of a part of the distal end side of the catheter 1 and the light irradiation device 2 in the living body lumen. A method of using the light irradiation system will be described with reference to FIGS. 1, 6, and 7.

First, an operator inserts a guide wire into a living body lumen. Next, the operator inserts a proximal end side of the guide wire from the opening 120o of the distal tip 120 of the catheter 1 illustrated in FIG. 1, via the through-hole 120h, through the lumen 110L, so that the guide wire protrudes from the opening 140o of the connector 140. Subsequently, the operator pushes the catheter 1 into the living body lumen along the guide wire, and the light transmitting portion 139 of the catheter 1 is delivered to a target site for light irradiation (for example, in the case of NIR-PIT, a vicinity of a cancer cell). Thus, by inserting the guide wire from the through-hole 120h formed in the distal tip 120 of the catheter 1, the operator can easily deliver the catheter 1 to the target site in the living body lumen. During delivery, the operator can position the catheter 1 in the living body lumen, while checking, in an X-ray image, the positions of the first marker portions 131 and 132 arranged in the vicinity of the light transmitting portion 139. Afterwards, the operator removes the guide wire from the catheter 1. It is noted that, when the catheter 1 is inserted into the living body lumen, body fluid flowing in the living body lumen (for example, blood flowing through a blood vessel) infiltrates the inside of the lumen 110L via the through-hole 120h of the distal tip 120.

Next, as illustrated in FIG. 6, the operator inserts the light irradiation device 2 from the opening 140o of the connector 140 of the catheter 1. The operator pushes the light irradiation device 2 toward the distal end side of the catheter 1, along the lumen 110L of the catheter 1. Here, as described above, the outer diameter phi 3 of the distal tip 220 (the large diameter portion) of the light irradiation device 2 is larger than the outer diameter phi 4 of the shaft 210 and the light irradiation portion 239 (FIG. 1: phi 3>phi 4). Therefore, as illustrated by white arrows in FIG. 7, body fluid 3 infiltrating the lumen 110L of the catheter 1 can be pushed out to the distal end side from the light irradiation portion 239 by the distal tip 220 distal to the light irradiation portion 239, and thus, the body fluid 3 can be removed from the vicinity of the light irradiation portion 239. In the illustrated example, the catheter 1 is formed with the through-hole 120h communicating the inside and outside of the tube in the longitudinal direction. Thus, the body fluid 3 pushed out by the distal tip 220 of the light irradiation device 2 can be ejected to the outside of the catheter 1 from the through-hole 120h.

Further, as described above, the inner diameter phi 2 of the catheter 1 is equal to or larger than the outer diameter phi 3 of the distal tip 220 of the light irradiation device 2 (FIG. 1: phi 3≤phi 2). Therefore, the light irradiation device 2 can be smoothly slid in the lumen 110L of the catheter 1. Further, as described above, the outer diameter phi 3 of the distal tip 220 of the light irradiation device 2 is larger than the opening diameter phi 1 of the through-hole 120h of the catheter 1 (FIG. 1: phi 1<phi 3). Therefore, a distal end surface 220e of the light irradiation device 2 abuts against the inner surface 120i of the distal tip 120 when the light irradiation device 2 is inserted into the catheter 1, and thus, it is possible to prevent the light irradiation device 2 from being advanced beyond the distal end side of the catheter 1 (FIG. 6).

After that, the operator aligns the light irradiation portion 239 with the light transmitting portion 139 in the direction of the axis O (X-axis direction), while checking, in an X-ray image, a positional relationship between the first marker portions 131 and 132 and the second marker portions 231 and 232. Thus, the laser light LT transmitted via the optical fiber 250 and emitted from the light irradiation portion 239 can be transmitted through the light transmitting portion 139 of the catheter 1 and emitted to living tissue on the outside. It is noted that, in the catheter 1 of the present embodiment, the light transmitting portion 139 is provided over the entire circumference (FIG. 3). Therefore, in the light irradiation system of the present embodiment, the operator only needs to achieve alignment between the light transmitting portion 139 and the light irradiation portion 239 in the direction of the axis O (X-axis direction), and does not need to achieve alignment between the light transmitting portion 139 and the light irradiation portion 239 in the circumferential direction.

As described above, according to the light irradiation system of the first embodiment, the light irradiation device 2 inserted into the catheter 1 for use includes the distal tip 220 (the large diameter portion) having the outer diameter phi 3 larger than the outer diameter phi 4 of the light irradiation portion 239. Therefore, when the light irradiation device 2 is inserted into the catheter 1, the body fluid 3 infiltrating the inside of the catheter 1 can be pushed out to the distal end side from the light irradiation portion 239 by the distal tip 220 distal to the light irradiation portion 239, and thus, the body fluid 3 can be removed from the vicinity of the light irradiation portion 239 (FIG. 7). As a result, according to the light irradiation device 2 of the first embodiment, it is possible to suppress light irradiation of the body fluid 3 in the catheter 1, and thus, the light irradiation device 2 can contribute to the suppression of coagulation of the body fluid 3 by light irradiation and the suppression of damage to living tissue.

Further, according to the light irradiation system of the first embodiment, the catheter 1 is provided with the through-hole 120h communicating the inside and outside of the tube, and thus, the body fluid 3 in the catheter 1 that is pushed out by the distal tip 220 (the large diameter portion) of the light irradiation device 2, can be ejected to the outside of the catheter 1 from the through-hole 120h (FIG. 7). Moreover, the through-hole 120h of the catheter 1 communicates between the inside and outside of the tube in the longitudinal direction of the catheter 1. Therefore, as described above in the method of using the light irradiation system, the through-hole 120h can also be used as an insertion port of the guide wire lumen for inserting the guide wire into the catheter 1.

Further, according to the light irradiation system of the first embodiment, it is possible to provide a light irradiation system in which the catheter 1 including the light transmitting portion 139 and the light irradiation device 2 including the light irradiation portion 239 are separately provided, and thus, the degree of freedom in designing the device can be improved and the range of procedures can be expanded. Moreover, the inner diameter phi 2 of the catheter 1 is equal to or larger than the outer diameter phi 3 of the distal tip 220 (the large diameter portion) of the light irradiation device 2, so that the light irradiation device 2 can be smoothly slid in the catheter 1. Further, in the catheter 1, using the single lumen 110L serving as both the guide wire lumen and a lumen for the light irradiation device 2 makes it possible to reduce the diameter of the catheter 1.

Second Embodiment

FIG. 8 is an explanatory diagram illustrating a configuration of a light irradiation system according to a second embodiment. The light irradiation system according to the second embodiment includes a catheter 1A and a light irradiation device 2A having configurations different from those of the first embodiment.

The catheter 1A includes a light transmitting portion 139A instead of the light transmitting portion 139. The light transmitting portion 139A is a plate-like member having an arc shape, and is fitted into a part of the shaft 110 to be joined to the shaft 110. Thus, the light transmitting portion 139A of the second embodiment is provided partially in the circumferential direction, and from the part in the circumferential direction, transmits light inside the shaft 110 to the outside. It is noted that the light transmitting portion 139A can be formed of a similar material to the light transmitting portion 139.

The light irradiation device 2A includes a light irradiation portion 239A instead of the light irradiation portion 239. The light irradiation portion 239A is a solid, substantially columnar member having a diameter that is substantially the same as the outer diameter of the shaft 210. The light irradiation portion 239A is joined to the shaft 210 at each of the proximal end side and the distal end side. Further, a surface of the light irradiation portion 239A at the proximal end side covers an exposed distal end of the core of the optical fiber 250. Therefore, in the light irradiation device 2A, the laser light LT generated by the laser light generator 3 is output, for irradiation, to the outside from the entire circumference of the light irradiation device 2A via the light irradiation portion 239A.

A method of using the light irradiation system of the second embodiment is similar to that of the first embodiment. In the light irradiation system of the second embodiment, as illustrated in FIG. 8, the light transmitting portion 139A of the catheter 1A is provided partially in the circumferential direction, whereas the light irradiation portion 239A of the light irradiation device 2A is provided over the entire circumference. Similarly to the first embodiment, in the light irradiation system according to the second embodiment, when the light irradiation device 2A is inserted into the catheter 1A, body fluid infiltrating the inside of the catheter 1A can be pushed out to the distal end side from the light irradiation portion 239A by the distal tip 220 distal to the light irradiation portion 239A, and thus, the body fluid can be removed from the vicinity of the light irradiation portion 239A.

FIG. 9 is an explanatory table showing combinations of the light transmitting portion 139 and the light irradiation portion 239. As shown in FIG. 9, any combination between the light transmitting portion 139 described in the first embodiment and the light transmitting portion 139A described in the second embodiment, and the light irradiation portion 239 described in the first embodiment and the light irradiation portion 239A described in the second embodiment is possible. That is, as shown in No. 1, the light irradiation system may have a configuration in which the light transmitting portion 139 (FIG. 1) that transmits light over the entire circumference and the light irradiation portion 239 (FIG. 1) that outputs irradiation light partially in the circumferential direction are combined. Further, as shown in No. 2, the light irradiation system may have a configuration in which the light transmitting portion 139A (FIG. 8) that transmits light partially in the circumferential direction and the light irradiation portion 239A (FIG. 8) that outputs irradiation light over the entire circumference are combined. Moreover, as shown in No. 3, the light irradiation system may have a configuration in which the light transmitting portion 139 (FIG. 1) that transmits light over the entire circumference and the light irradiation portion 239A (FIG. 8) that outputs irradiation light over the entire circumference are combined. Further, as shown in No. 4, the light irradiation system may have a configuration in which the light transmitting portion 139A (FIG. 8) that transmits light partially in the circumferential direction and the light irradiation portion 239 (FIG. 1) that outputs irradiation light partially in the circumferential direction are combined. According to the light irradiation system of the second embodiment described above, an effect similar to the first embodiment described above can be also achieved.

Third Embodiment

Figure 10:
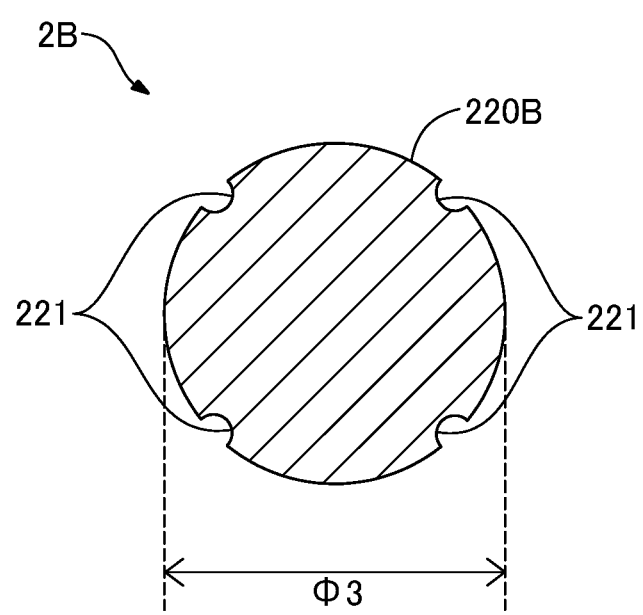
FIG. 10 is an explanatory diagram illustrating a transverse sectional configuration of a distal tip according to a third embodiment.

FIG. 10 is an explanatory diagram illustrating a transverse sectional configuration of a distal tip 220B according to a third embodiment (FIG. 1: cross-sectional configuration along line C-C). The light irradiation system according to the third embodiment includes the catheter 1 described in the first embodiment, and a light irradiation device 2B having a configuration different from that of the first embodiment.

The light irradiation device 2B includes the distal tip 220B instead of the distal tip 220. Similarly to the first embodiment, the distal tip 220B is a member having a substantially columnar shape extending in the longitudinal direction of the light irradiation device 2B. Groove portions 221 extending in the longitudinal direction (the direction of the axis O) are formed on an outer peripheral surface of the distal tip 220B. The groove portions 221 extend linearly from the distal end surface 220e of the distal tip 220B to a proximal end surface (FIG. 1: an end surface on the +X-axis side), and enable the flow of gas (for example, air) between the distal end side and the proximal end side of the distal tip 220B. An opening area of the groove portions 221 can be determined freely. However, it is preferable that the opening area of the groove portions 221 has a size at which the body fluid 3 (FIG. 7) does not easily flow in the catheter 1, and gas can flow in the catheter 1. In the illustrated example, four of the groove portions 221 arranged at intervals of about 90 degrees in the circumferential direction are formed on the outer peripheral surface of the distal tip 220B.

As described above, the configuration of the distal tip 220B of the light irradiation device 2B can be modified in various ways, and one or a plurality of the groove portions 221 may be formed on the outer peripheral surface of the distal tip 220B. The number, arrangement, transverse sectional shape, and opening area of the groove portions 221 can be determined freely. Further, the groove portions 221 are arranged on the outer peripheral surface of the distal tip 220B, and may not be linear as long as the groove portions 221 extend in the longitudinal direction of the light irradiation device 2B, and may have a wavelike shape or a bellows shape. According to the light irradiation system of the third embodiment described above, an effect similar to the first embodiment described above can be also achieved. Further, according to the light irradiation system of the third embodiment, the groove portions 221 extending in the longitudinal direction are formed on the outer peripheral surface of the distal tip 220B (the large diameter portion) of the light irradiation device 2B. Therefore, if the groove portions 221 are caused to function as air discharge holes, the light irradiation device 2B can be smoothly slid (moved in the longitudinal direction) in the catheter 1.

Fourth Embodiment

Figure 11:
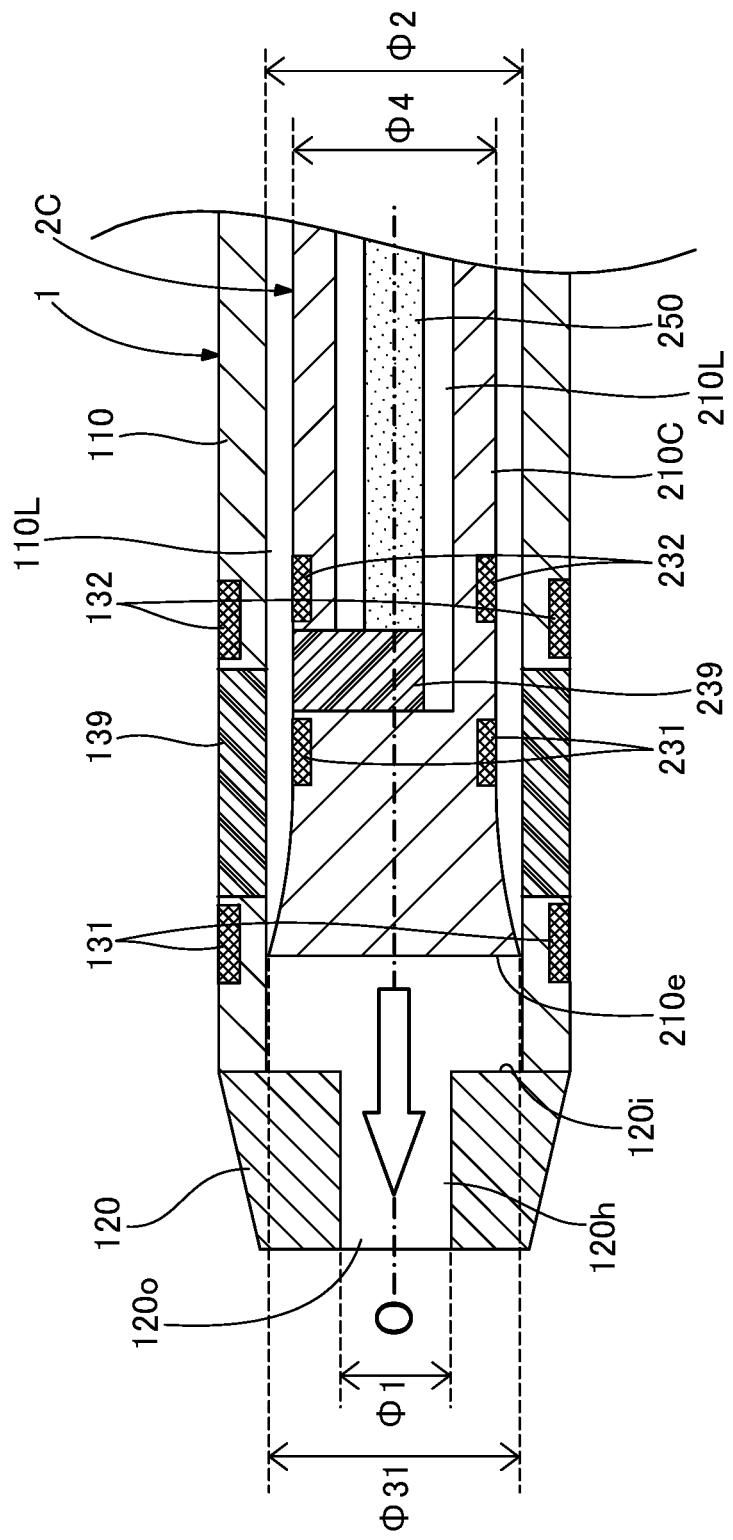
FIG. 11 is an explanatory diagram illustrating a configuration of a light irradiation system according to a fourth embodiment.

FIG. 11 is an explanatory diagram illustrating a configuration of a light irradiation system according to a fourth embodiment. The light irradiation system according to the fourth embodiment includes the catheter 1 described in the first embodiment, and a light irradiation device 2C having a configuration different from that of the first embodiment.

The light irradiation device 2C does not include the distal tip 220 and includes a shaft 210C instead of the shaft 210. A part of the shaft 210C distal to the light irradiation portion 239 functions as a large diameter portion. Specifically, a part of the shaft 210C distal to the light irradiation portion 239 has a tapered shape having the outer diameter increasing from the proximal end side toward the distal end side. An outer diameter phi 31 of a distal end surface 210e of the shaft 210C is larger than the outer diameter phi 4 of the light irradiation portion 239 (phi 31>phi 4). Further, it is preferable that the outer diameter phi 31 of the distal end surface 210e of the shaft 210C is larger than the opening diameter phi 1 of the through-hole 120h of the catheter 1 and is equal to or less than the inner diameter phi 2 of the shaft 110 and the light transmitting portion 139 of the catheter 1 (phi 1<phi 31≤phi 2).

As described above, the configuration of the light irradiation device 2C can be modified in various ways, and the distal tip 220 described in the first embodiment may not be provided, and a large diameter portion may be formed in a part of the shaft 210C. The large diameter portion may be provided at any position in the shaft 210C, as long as the position is distal to the light irradiation portion 239, and is not limited to the distal end surface 210e. According to the light irradiation system of the fourth embodiment described above, an effect similar to the first embodiment described above can be also achieved. Further, according to the light irradiation system of the fourth embodiment, the number of parts in the light irradiation device 2C can be reduced, and thus, it is possible to reduce the manufacturing cost of the light irradiation device 2C.

Fifth Embodiment

Figure 12:
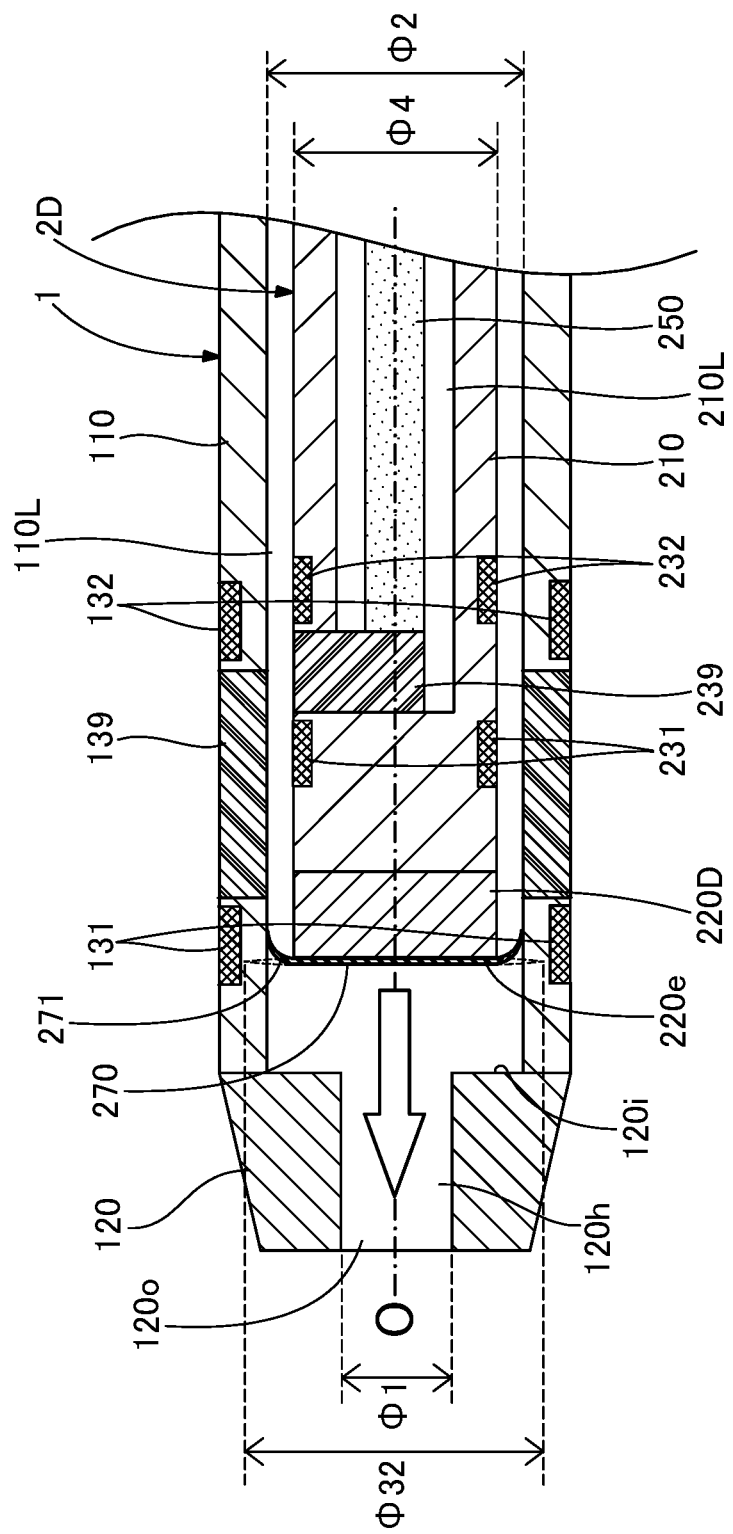
FIG. 12 is an explanatory diagram illustrating a configuration of a light irradiation system according to a fifth embodiment.

FIG. 12 is an explanatory diagram illustrating a configuration of a light irradiation system according to a fifth embodiment. The light irradiation system according to the fifth embodiment includes the catheter 1 described in the first embodiment, and a light irradiation device 2D having a configuration different from that of the first embodiment.

The light irradiation device 2D includes a distal tip 220D instead of the distal tip 220, and further includes a valve body 270. The distal tip 220D has an outer diameter phi 4 that is substantially the same as that of the shaft 210 and the light irradiation portion 239, and the large diameter portion is not formed. The valve body 270 is a substantially circular plate-like member formed of an elastic body, and one side thereof is joined to the distal end surface 220e of the distal tip 220D. For the joining, any bonding agent such as an epoxy-based adhesive may be used. An outer diameter phi 32 of the valve body 270 is larger than the outer diameter phi 4 of the distal tip 220, the shaft 210, and the light irradiation portion 239 (phi 32>phi 4). Further, the outer diameter phi 32 of the valve body 270 is larger than the opening diameter phi 1 of the through-hole 120h of the catheter 1 and is larger than the inner diameter phi 2 of the shaft 110 and the light transmitting portion 139 of the catheter 1 (phi 1, phi 2<phi 32).

According to the light irradiation system of the fifth embodiment, when the light irradiation device 2D is inserted into the catheter 1, an outer peripheral portion 271 of the valve body 270 bends as illustrated in the drawing to move along an inner wall of the shaft 110 of the catheter 1. As a result, body fluid infiltrating the lumen 110L of the catheter 1 can be pushed out more effectively. In the present embodiment, the valve body 270 functions as a "large diameter portion".

As described above, the configuration of the light irradiation device 2D can be modified in various ways, and the large diameter portion may be formed by using a means other than the distal tip 220D (for example, the valve body 270 described above). Above, it is assumed that the valve body 270 is joined to the distal tip 220D, however, the valve body 270 may be joined to a distal end surface of the shaft 210 (in this case, the distal tip 220D may be omitted). Further, the valve body 270 may be formed in a part of the distal tip 220D or a part of the shaft 210. According to the light irradiation system of the fifth embodiment described above, an effect similar to the first embodiment described above can be achieved.

Sixth Embodiment

Figure 13:
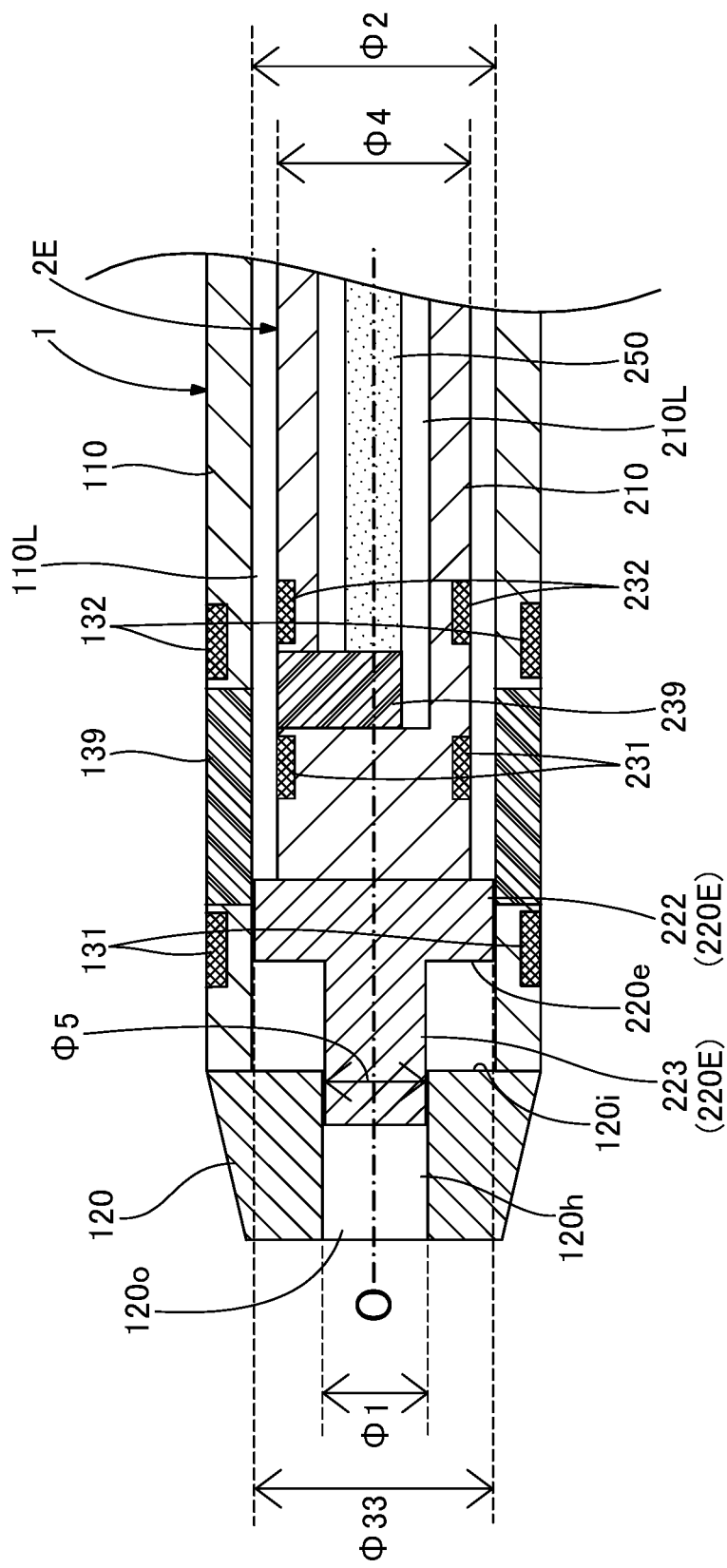
FIG. 13 is an explanatory diagram illustrating a configuration of a light irradiation system according to a sixth embodiment.

FIG. 13 is an explanatory diagram illustrating a configuration of a light irradiation system according to a sixth embodiment. The light irradiation system according to the sixth embodiment includes the catheter 1 described in the first embodiment, and a light irradiation device 2E having a configuration different from that of the first embodiment.

The light irradiation device 2E includes a distal tip 220E instead of the distal tip 220. The distal tip 220E includes a large diameter portion 222 and a protruding portion 223. The large diameter portion 222 has a configuration similar to that of the distal tip 220 described in the first embodiment. That is, the large diameter portion 222 is a substantially columnar member extending in the longitudinal direction of the light irradiation device 2E, and an outer diameter phi 33 of the large diameter portion 222 is larger than the outer diameter phi 4 of the shaft 210 and the light irradiation portion 239 (phi 33>phi 4). Further, the outer diameter phi 33 of the large diameter portion 222 is larger than the opening diameter phi 1 of the through-hole 120h of the catheter 1 and is equal to or less than the inner diameter phi 2 of the shaft 110 and the light transmitting portion 139 of the catheter 1 (phi 1<phi 3≤phi 2).

The protruding portion 223 is a member having a substantially columnar shape extending in the longitudinal direction of the light irradiation device 2E and having a smaller diameter than the large diameter portion 222. The protruding portion 223 is joined to the distal end surface 220e of the large diameter portion 222 in a state where a center of the protruding portion 223 and a center of the through-hole 120h of the catheter 1 are aligned with each other. For the joining, any bonding agent such as an epoxy-based adhesive may be used. It is noted that the large diameter portion 222 and the protruding portion 223 may be integrally formed. An outer diameter phi 5 of the protruding portion 223 is equal to or less than the opening diameter phi 1 of the through-hole 120h of the catheter 1 (phi 5≤phi 1). According to the light irradiation system of the sixth embodiment, when the light irradiation device 2E is inserted into the catheter 1, the protruding portion 223 engages, as illustrated in the drawing, with the through-hole 120h of the catheter 1, so that the light irradiation device 2E and the catheter 1 can be positioned in a long axis direction (the direction of the axis O).

As described above, the configuration of the light irradiation device 2E can be modified in various ways, and in addition to the large diameter portion 222, the protruding portion 223 to be engaged with the through-hole 120h of the catheter 1 may further be provided in a distal end portion of the light irradiation device 2E. According to the light irradiation system of the sixth embodiment described above, an effect similar to the first embodiment described above can be achieved. Further, according to the light irradiation system of the sixth embodiment, when the light irradiation device 2E is inserted into the catheter 1, the protruding portion 223 formed on the distal end side of the large diameter portion 222 of the light irradiation device 2E is engaged with the through-hole 120h of the catheter 1, so that the light irradiation device 2E and the catheter 1 can be easily positioned in the long axis direction.

Seventh Embodiment

Figure 14:
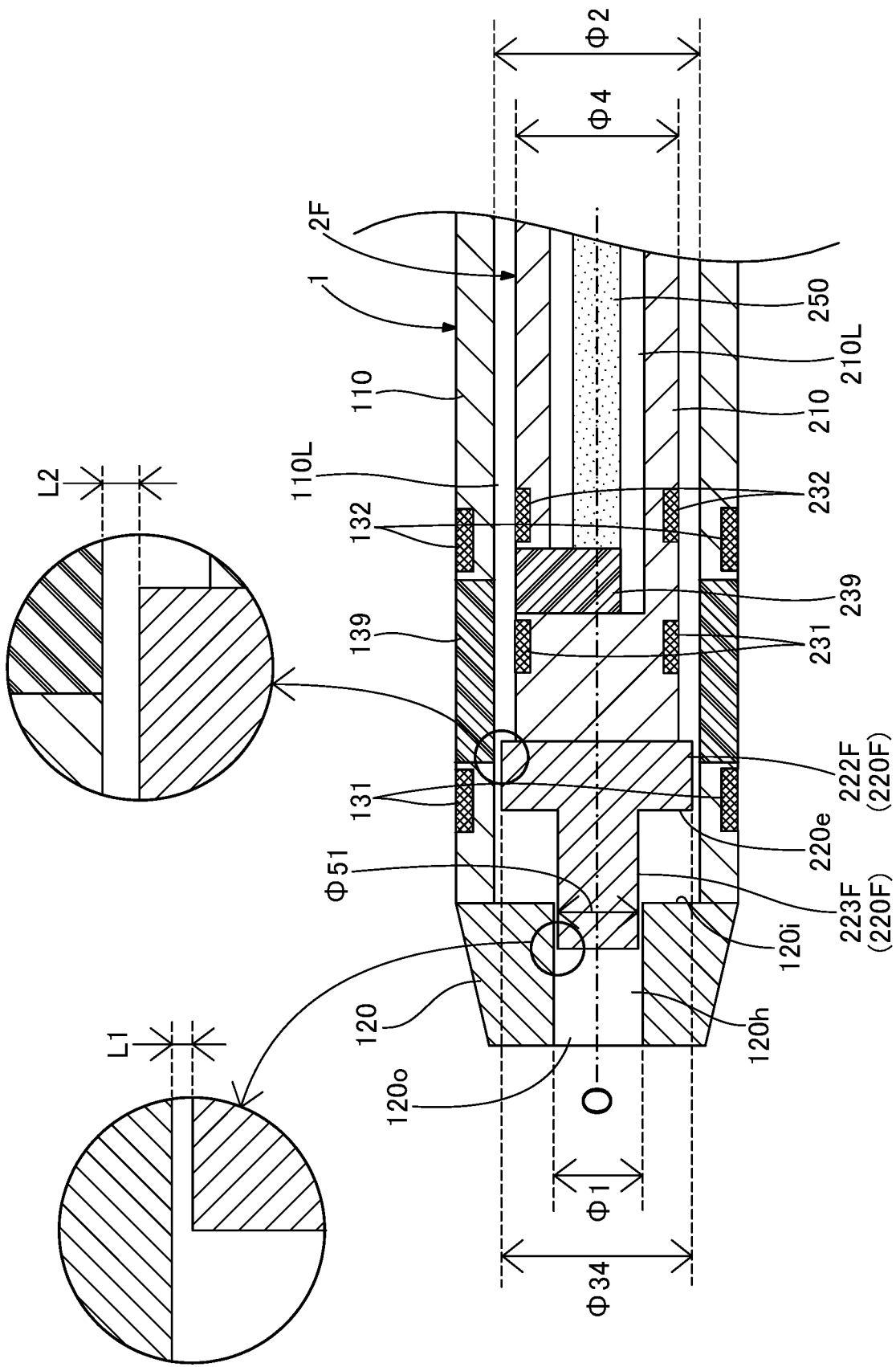
FIG. 14 is an explanatory diagram illustrating a configuration of a light irradiation system according to a seventh embodiment.

FIG. 14 is an explanatory diagram illustrating a configuration of a light irradiation system according to a seventh embodiment. The light irradiation system according to the seventh embodiment includes the catheter 1 described in the first embodiment, and a light irradiation device 2F having a configuration different from that of the sixth embodiment.

The light irradiation device 2F includes a large diameter portion 222F instead of the large diameter portion 222, and a protruding portion 223F instead of the protruding portion 223. The large diameter portion 222F has an outer diameter phi 34 different from the outer diameter described in the sixth embodiment. Similarly, the protruding portion 223F has an outer diameter phi 51 different from the outer diameter described in the sixth embodiment. The outer diameter phi 34 of the large diameter portion 222F and the outer diameter phi 51 of the protruding portion 223F have sizes satisfying Expression (1) below.

$$\{(phi\ 1 - phi\ 51)/2\} < \{(phi\ 2 - phi\ 34)/2\} \tag{1}$$

In other words, in the light irradiation system of the seventh embodiment, in a state where the light irradiation device 2F is inserted into the catheter 1 and the protruding portion 223F of the light irradiation device 2F is engaged with the through-hole 120h of the catheter 1, a length L1 between the outer peripheral surface of the protruding portion 223F and the inner peripheral surface of the through-hole 120h ((phi 1−phi 51)/2) is shorter than a length L2 between the outer peripheral surface of the large diameter portion 222F and the inner peripheral surface of the catheter 1 ((phi 2−phi 34)/2).

As described above, the configuration of the light irradiation device 2E can be modified in various ways, and in a configuration including the large diameter portion 222F and the protruding portion 223F, sizes of a gap between the large diameter portion 222F and the catheter 1 and a gap between the protruding portion 223F and the through-hole 120h may be different from each other. According to the light irradiation system of the seventh embodiment described above, an effect similar to the first and sixth embodiments described above can be achieved. Further, according to the light irradiation system of the seventh embodiment, the slidability of the light irradiation device 2F in the catheter 1 can be improved, and the light irradiation device 2F and the catheter 1 can be surely positioned in the long axis direction.

Eighth Embodiment

Figure 15:
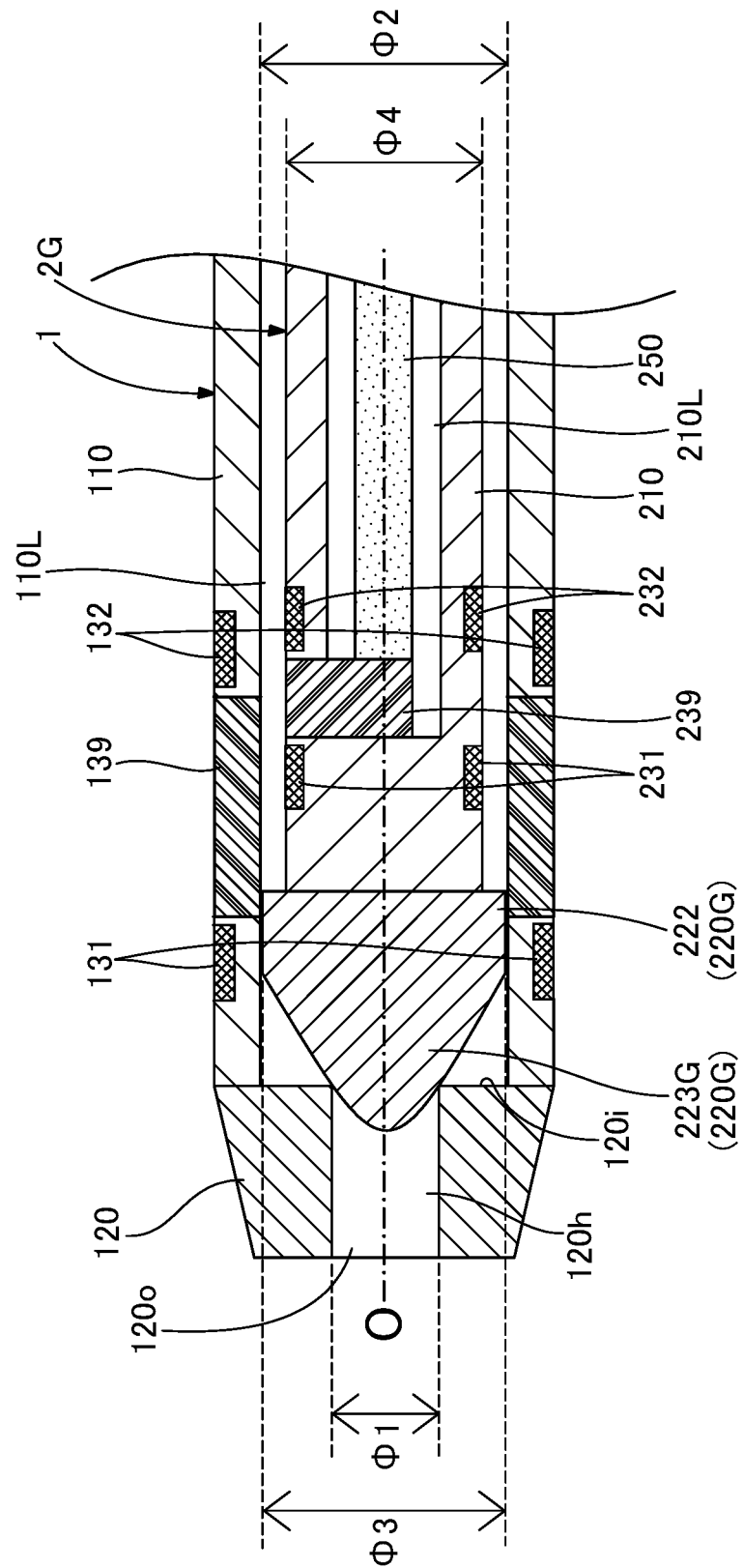
FIG. 15 is an explanatory diagram illustrating a configuration of a light irradiation system according to an eighth embodiment.

FIG. 15 is an explanatory diagram illustrating a configuration of a light irradiation system according to an eighth embodiment. The light irradiation system according to the eighth embodiment includes the catheter 1 described in the first embodiment, and a light irradiation device 2G having a configuration different from that of the sixth embodiment.

The light irradiation device 2G includes a protruding portion 223G instead of the protruding portion 223. The protruding portion 223G is a member having a substantially conical shape extending in the longitudinal direction of the light irradiation device 2G. As for the protruding portion 223G, a bottom surface of the protruding portion 223G is joined to the distal end surface 220e of the large diameter portion 222 in a state where the rotation axis of the protruding portion 223G and the center of the through-hole 120h of the catheter 1 are aligned with each other. It is noted that the large diameter portion 222 and the protruding portion 223G may be integrally formed.

As described above, the configuration of the light irradiation device 2G can be modified in various ways, and the shape of the protruding portion 223G to be engaged with the through-hole 120h of the catheter 1 is not limited to the conical shape, and various shapes such as a columnar shape and a triangular pyramid shape can be adopted. According to the light irradiation system of the eighth embodiment described above, an effect similar to the first and sixth embodiments described above can be achieved. Further, according to the light irradiation system of the eighth embodiment, the protruding portion 223G and the through-hole 120h can be engaged with each other at any position in accordance with the inner diameter of the through-hole 120h of the catheter 1.

Ninth Embodiment

Figure 16:
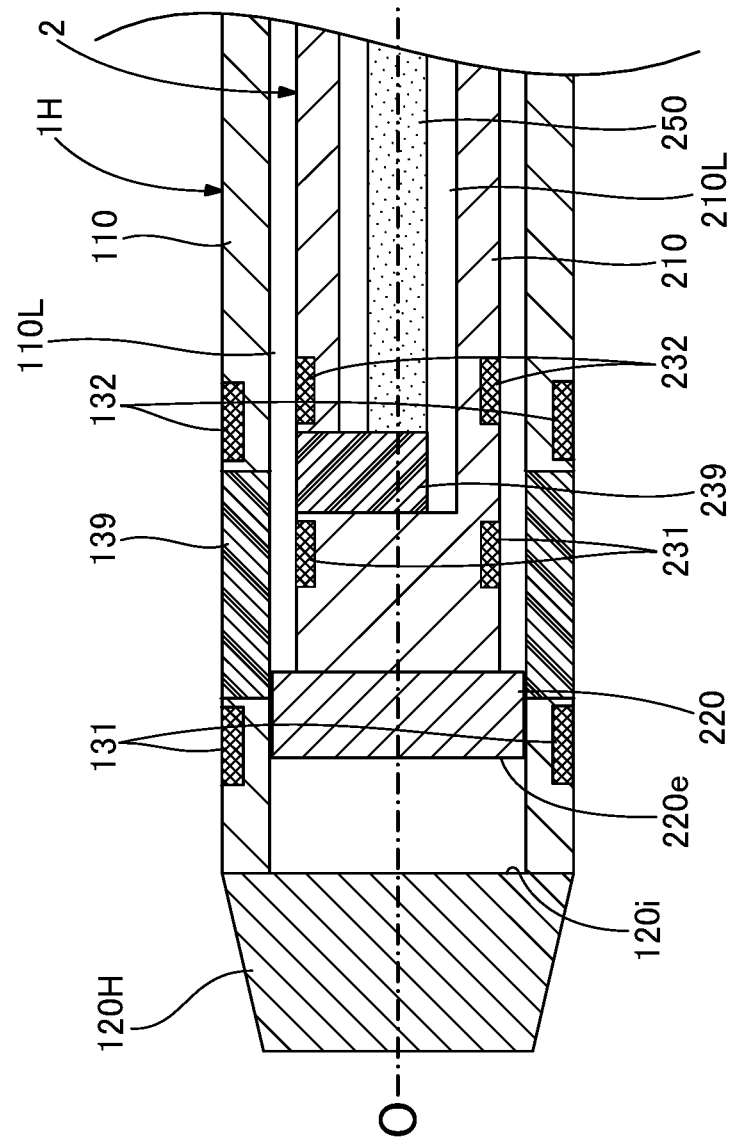
FIG. 16 is an explanatory diagram illustrating a configuration of a light irradiation system according to a ninth embodiment.

FIG. 16 is an explanatory diagram illustrating a configuration of a light irradiation system according to a ninth embodiment. The light irradiation system according to the ninth embodiment includes a catheter 1H having a configuration different from that of the first embodiment, and the light irradiation device 2 described in the first embodiment. The catheter 1H includes a distal tip 120H instead of the distal tip 120. The through-hole 120h described in the first embodiment is not formed in the distal tip 120H.

Also in the light irradiation system of the ninth embodiment, when the light irradiation device 2 is inserted into the catheter 1H, body fluid infiltrating the lumen 110L of the catheter 1H can be pushed out to the distal end side from the light irradiation portion 239 by the distal tip 220 distal to the light irradiation portion 239, and thus, the body fluid can be removed from the vicinity of the light irradiation portion 239. As described above, the configuration of the catheter 1H can be modified in various ways, and the configuration may include a distal tip 220H not including the through-hole 120h. According to the light irradiation system of the ninth embodiment described above, an effect similar to the first embodiment described above can be achieved.

Tenth Embodiment

Figure 17:
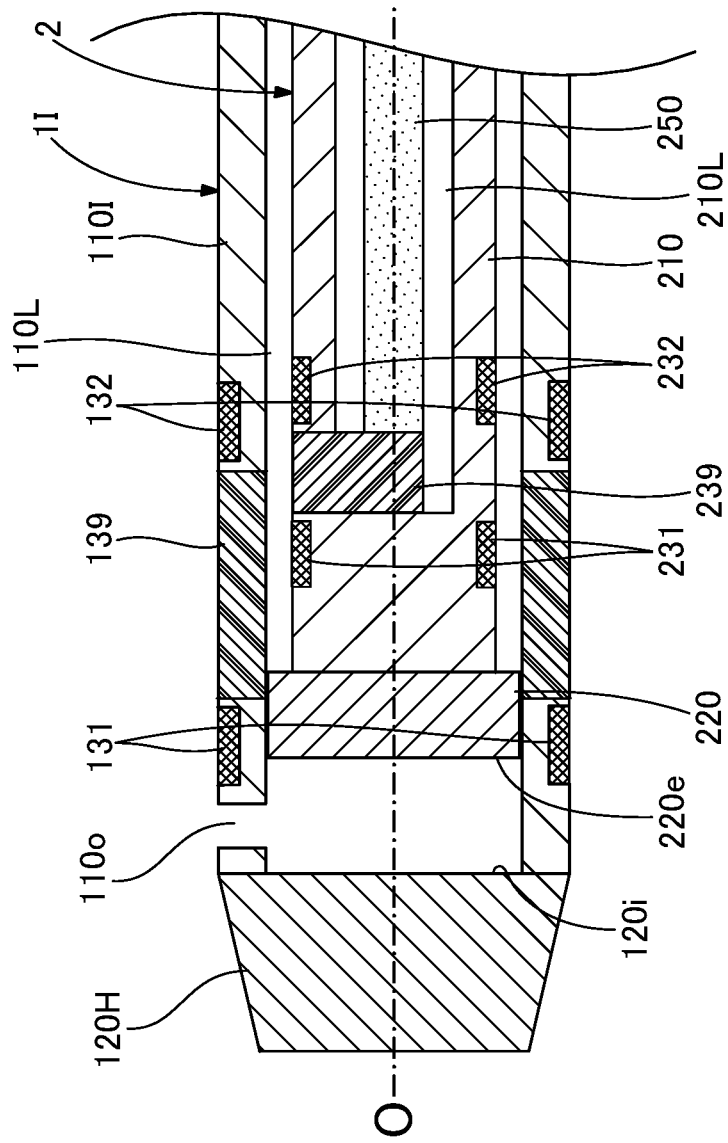
FIG. 17 is an explanatory diagram illustrating a configuration of a light irradiation system according to a tenth embodiment.

FIG. 17 is an explanatory diagram illustrating a configuration of a light irradiation system according to a tenth embodiment. The light irradiation system according to the tenth embodiment includes a catheter 1I having a configuration different from that of the ninth embodiment, and the light irradiation device 2 described in the first embodiment. The catheter 1I includes a shaft 110I instead of the shaft 110. The shaft 110I is formed with a through-hole 110o communicating the inside and outside of the shaft 110 at any position distal to the light transmitting portion 139.

Also in the light irradiation system of the tenth embodiment, when the light irradiation device 2 is inserted into the catheter 1I, body fluid infiltrating the lumen 110L of the catheter 1I can be pushed out to the distal end side from the light irradiation portion 239 by the distal tip 220 distal to the light irradiation portion 239, and thus, the body fluid can be removed from the vicinity of the light irradiation portion 239. Further, the body fluid pushed out by the distal tip 220 of the light irradiation device 2 can be ejected to the outside of the catheter 1I from the through-hole 110o of the shaft 110I. As described above, the configuration of the catheter 1I can be modified in various ways, and the through-hole 110o communicating the inside and outside of the tube may be provided in a separate member different from the distal tip 220H, such as the shaft 110I. According to the light irradiation system of the tenth embodiment described above, an effect similar to the first embodiment described above can be achieved.

<Modifications of Embodiment>

The disclosed embodiments are not limited to the above-described embodiments, and may be implemented in various modes without departing from the spirit of the disclosed embodiments. The following modifications can be applied, for example.

[First Modification]

In the first to tenth embodiments described above, examples of the configurations of the catheters 1, 1A, 1H, and 1I and the light irradiation devices 2 and 2A to 2G are illustrated. However, the configurations of the catheter 1 and the light irradiation device 2 can be modified in various ways.

For example, a reinforcing layer formed of a braided body or a coil body may be embedded in the shaft 110 of the catheter 1 and the shaft 210 of the light irradiation device 2. Thus, it is possible to improve the torquability and the shape retention of the catheter 1 and the light irradiation device 2. For example, a coating formed of a hydrophilic or hydrophobic resin may be applied to the outer surface of the catheter 1 and the outer surface of the light irradiation device 2. Thus, the slidability of the catheter 1 in the living body lumen can be improved. Further, the slidability of the light irradiation device 2 in the lumen 110L of the catheter 1 can be improved. Moreover, the outer surface of the catheter 1 or the outer surface of the light irradiation device 2 may be coated with an antithrombotic material such as heparin. This makes it possible to suppress a decrease in laser output due to thrombus adhesion to the inner and outer surfaces of the catheter 1 and the outer surface of the light irradiation device 2 caused by the irradiation with the emission light (laser light) LT.

For example, the catheter 1 may include an expansion portion expandable in a radial direction (YZ-direction). For example, a balloon formed of a flexible thin film or a mesh body having wires arranged in a mesh shape can be used as the expansion portion. The expansion portion may be provided on at least one of the distal end side of the light transmitting portion 139 and the proximal end side of the light transmitting portion 139 in the shaft 110. Thus, after the catheter 1 is positioned in the living body lumen, the catheter 1 can be fixed in the living body lumen by expanding the expansion portion. Further, if a balloon is used as the expansion portion, the bloodstream at the site being irradiated with light can be blocked, and thus, it is possible to prevent that the bloodstream blocks the light.

For example, the catheter 1 may be configured as a multi-lumen catheter including a plurality of lumens different from the lumen 110L. Similarly, the light irradiation device 2 may be configured as a multi-lumen catheter including a separate lumen different from the lumen 210L into which the optical fiber 250 is inserted. In this case, the shaft 210 can be formed by using a hollow member having a substantially hollow cylindrical shape, and the distal tip 220 can be provided with a through-hole extending along the direction of the axis O.

For example, the inner surface of the distal tip 120 of the catheter 1 and the outer surface of the distal tip 220 of the light irradiation device 2 may be formed of a magnetic material and may be configured to attract each other. Thus, as illustrated in FIG. 6, a state where the light irradiation device 2 is inserted into the catheter 1 and the distal tip 220 is pressed against the distal tip 120 can be easily maintained. For example, the distal tip 120 of the catheter 1 may be omitted, and a configuration in which the distal end side of the shaft 110 is open may be adopted. Thus, when the light irradiation device 2 is inserted into the catheter 1, body fluid pushed out by the distal tip 220 (the large diameter portion) can be ejected to the outside of the catheter 1 from an open portion on the distal end side of the shaft 110.

[Second Modification]

In the first to tenth embodiments described above, examples of the configurations of the distal tips 120 and 120H of the catheter 1 and the distal tips 220, 220B, 220D, 220E, and 220H (large diameter portions) of the light irradiation device 2 are illustrated. However, the configurations of the distal tip 120 of the catheter 1 and the distal tip 220 of the light irradiation device 2 can be modified in various ways. For example, the outer diameter phi 3 of the distal tip 220 (the large diameter portion) of the light irradiation device 2 may be larger than the inner diameter phi 2 of the shaft 110 and the light transmitting portion 139 of the catheter 1. In this case, to improve the slidability of the light irradiation device 2 when the light irradiation device 2 is inserted into the catheter 1, the distal tip 220 is preferably made of a material having an outer diameter expandable and contractible (for example, an elastic body and a porous body).

For example, a mesh member may be arranged in the through-hole 120h of the distal tip 120 of the catheter 1. Thus, a coagulant body fluid (for example, a thrombus) generated in the catheter 1 can be captured while allowing for the guide wire to be inserted into the catheter 1. As a result, body fluid pushed out by the distal tip 220 (the large diameter portion) of the light irradiation device 2 can be ejected to the outside of the catheter 1 while removal of the coagulant body fluid to the outside can be suppressed.

[Third Modification]

In the first to tenth embodiments described above, examples of the configurations of the light transmitting portions 139 and 139A and the light irradiation portions 239 and 239A are illustrated. However, the configurations of the light transmitting portion 139 and the light irradiation portion 239 can be changed in various ways. For example, the light transmitting portion 139 may be formed of a radiopaque material, to integrally form the light transmitting portion 139 and the first marker portions 131 and 132. Similarly, the light irradiation portion 239 may be formed of a radiopaque material, to integrally form the light irradiation portion 239 and the second marker portions 231 and 232.

For example, the light transmitting portion 139 may be formed by thinning a part of the shaft 110. For example, at least one of the light transmitting portion 139 and the light irradiation portion 239 may be formed as a notch (a through-hole communicating the inside and outside of the shaft) formed in the shaft 110 or the shaft 210. Thus, the light transmitting portion 139 and the light irradiation portion 239 can be easily formed. Further, if the light transmitting portion 139 is formed as a notch, body fluid pushed out by the distal tip 220 (the large diameter portion) when the light irradiation device 2 is inserted into the catheter 1, can be ejected to the outside of the catheter 1 from the light transmitting portion 139 (the notch).

For example, ranges in which the light transmitting portion 139 is provided in the direction of the axis O (the X-axis direction) and the circumferential direction (a YZ-axis direction), and ranges in which the light irradiation portion 239 is provided in the direction of the axis O and the circumferential direction can be modified to any range. Specifically, the light transmitting portion 139 may be provided in a wide range in the direction of the axis O, for example.

For example, the catheter 1 may further include a separate marker portion arranged at any position, such as the distal end side of the light transmitting portion 139 or the proximal end side of the light transmitting portion 139. For example, the light irradiation device 2 may further include a separate marker portion arranged at any position, such as the distal end side of the light irradiation portion 239 or the proximal end side of the light irradiation portion 239. The marker portions of the catheter 1 and the light irradiation device 2 may have any shape, including a shape wholly or partly extending in the circumferential direction (the YZ-direction), a shape extending in the direction of the axis O (the X-axis direction), and a shape surrounding a periphery of the shaft. Further, the distal tip 120 of the catheter 1 and the distal tip 220 of the light irradiation device 2 may be configured as a marker portion.

For example, the distal end surface of the optical fiber 250 may be diagonally cut, and this distal end surface may be configured as the light irradiation portion 239. For example, a light-reflecting mirror installed at an angle with respect to a cutting plane of the optical fiber 250 (a cutting plane provided perpendicular to the direction of the axis O) may be provided for use as the light irradiation portion 239. For example, the optical fiber 250 may not be inserted into the shaft 210 and may be joined to the outer surface of the shaft 210. For example, the shaft 210 may not include the lumen 210L, and the shaft 210 may be provided to contact the outer surface of the optical fiber 250 and cover the outer surface of the optical fiber 250.

[Fourth Modification]

The configurations of the catheters 1, 1A, 1H, and 1I and the light irradiation devices 2 and 2A to 2G of the first to tenth embodiments, and the configurations of the catheters 1, 1A, 1H, and 1I and the light irradiation devices 2 and 2A to 2G of the first to third modifications described above may be appropriately combined. For example, in the catheter 1 and the light irradiation device 2 employing various combinations of the light transmitting portion 139 and the light irradiation portion 239 described in the second embodiment (FIG. 9), a configuration including the distal tips and the shafts described in each of the third to tenth embodiments may be adopted. For example, the light irradiation devices 2B, 2C, and 2D described in the third, fourth, and fifth embodiments may be used in combination with the catheters 1H and 1I described in the ninth and tenth embodiments.

Although the aspects have been described based on the embodiments and the modifications, the embodiments of the above-described aspects are for facilitating understanding of the aspects, and do not limit the aspects. The aspects can be modified and improved without departing from the spirit of the aspects and the scope of the claims, and equivalent aspects are included in the aspects. Further, unless a technical feature is described as essential in the present specification, the technical feature may be omitted as appropriate.

DESCRIPTION OF REFERENCE NUMERALS 1, 1A, 1H, 1I . . . Catheter
2, 2A to 2G . . . Light irradiation device
3 . . . . Laser light generator
110, 110I . . . Shaft
110o . . . Through-hole
120, 120H . . . Distal tip
120h . . . Through-hole
131, 132 . . . First marker portion
139, 139A . . . Light transmitting portion
140 . . . Connector
141 . . . Connection portion
142 . . . Blade
210, 210C . . . Shaft
220, 220B, 220D, 220E, 220H . . . Distal tip
221 . . . Groove portion
222, 222F . . . Large diameter portion
223, 223F, 223G . . . Protruding portion
231, 232 . . . Second marker portion
239, 239A . . . Light irradiation portion
240 . . . Connector
241 . . . Connection portion
242 . . . Blade
250 . . . Optical fiber
270 . . . Valve body
271 . . . Outer peripheral portion

What is claimed is:

1. A light irradiation device having an elongated shape and configured to be inserted into a catheter, the light irradiation device comprising:
 a light irradiation portion provided on a distal end side of the light irradiation device and configured to output irradiation light to outside of the light irradiation device; and
 a large diameter portion positioned distal to the light irradiation portion and having an outer diameter larger than an outer diameter of the light irradiation portion,
 wherein the large diameter portion is configured to push out body fluid infiltrating a lumen of the catheter toward a distal end side from the light irradiation portion when the light irradiation device is inserted into the catheter.

2. The light irradiation device according to claim 1, wherein
 the large diameter portion has a columnar shape extending in a longitudinal direction of the light irradiation device, and a groove portion extending in the longitudinal direction is formed on an outer peripheral surface of the large diameter portion.

3. A light irradiation system comprising:
 the light irradiation device according to claim 1; and
 a catheter having an elongated tube configured to receive the light irradiation device, wherein the catheter includes:
  a light transmitting portion provided on a distal end side of the catheter and configured to transmit light inside the tube to outside of the catheter, and
  an inner diameter of the catheter is equal to or larger than the outer diameter of the large diameter portion of the light irradiation device.

4. The light irradiation device according to claim 1, wherein the large diameter portion positioned distal to the light irradiation portion has an outer diameter larger than an outer diameter of the light irradiation device at a position where the light irradiation portion is provided.

5. The light irradiation system according to claim 3, wherein the catheter further includes:
 a through-hole positioned distal to the light transmitting portion and communicating between an inside and an outside of the tube.

6. The light irradiation system according to claim 5, wherein in the catheter,
 the through-hole communicates between the inside and the outside of the tube in a longitudinal direction of the catheter, and
 an opening diameter of the through-hole is smaller than the outer diameter of the large diameter portion of the light irradiation device.

7. The light irradiation system according to claim 6, wherein in the light irradiation device,
 a protruding portion configured to engage the through-hole of the catheter is provided on a distal end side of the large diameter portion.

8. The light irradiation system according to claim 7, wherein
 in a state where the light irradiation device is inserted into the catheter and the protruding portion engages the through-hole,
 a distance between an outer peripheral surface of the protruding portion and an inner peripheral surface of the through-hole in a radial direction of the catheter is shorter than a distance between an outer peripheral surface of the large diameter portion and an inner peripheral surface of the catheter in the radial direction.

9. The light irradiation system according to claim 6, wherein in the light irradiation device,
 a protruding portion configured to be inserted into the through-hole of the catheter is provided on a distal end side of the large diameter portion.

10. The light irradiation system according to claim 3, wherein the inner diameter of the catheter is equal to the outer diameter of the large diameter portion of the light irradiation device.

11. A light irradiation device having an elongated shape and configured to be inserted into a catheter, the light irradiation device comprising:
 a light irradiation portion provided on a distal end side of the light irradiation device and configured to output irradiation light to outside of the light irradiation device; and
 a large diameter portion positioned distal to the light irradiation portion and having an outer diameter larger than an outer diameter of the light irradiation device at a position where the light irradiation portion is provided.

12. The light irradiation device according to claim 11, wherein
 the large diameter portion has a columnar shape extending in a longitudinal direction of the light irradiation device, and a groove portion extending in the longitudinal direction is formed on an outer peripheral surface of the large diameter portion.

13. A light irradiation system comprising:
 the light irradiation device according to claim 12; and
 a catheter having an elongated tube configured to receive the light irradiation device, wherein the catheter includes:
  a light transmitting portion provided on a distal end side of the catheter and configured to transmit light inside the tube to outside of the catheter, and an inner diameter of the catheter is equal to or larger than the outer diameter of the large diameter portion of the light irradiation device.

14. A light irradiation system comprising:
the light irradiation device according to claim 11; and
a catheter having an elongated tube configured to receive the light irradiation device, wherein the catheter includes:
   a light transmitting portion provided on a distal end side of the catheter and configured to transmit light inside the tube to outside of the catheter, and
   an inner diameter of the catheter is equal to or larger than the outer diameter of the large diameter portion of the light irradiation device.

15. The light irradiation system according to claim 14, wherein the catheter further includes:
a through-hole positioned distal to the light transmitting portion and communicating between an inside and an outside of the tube.

16. The light irradiation system according to claim 15, wherein in the catheter,
the through-hole communicates between the inside and the outside of the tube in a longitudinal direction of the catheter, and
an opening diameter of the through-hole is smaller than the outer diameter of the large diameter portion of the light irradiation device.

17. The light irradiation system according to claim 16, wherein in the light irradiation device,
a protruding portion configured to engage the through-hole of the catheter is provided on a distal end side of the large diameter portion.

18. The light irradiation system according to claim 17, wherein
in a state where the light irradiation device is inserted into the catheter and the protruding portion engages the through-hole,
a distance between an outer peripheral surface of the protruding portion and an inner peripheral surface of the through-hole in a radial direction of the catheter is shorter than a distance between an outer peripheral surface of the large diameter portion and an inner peripheral surface of the catheter in the radial direction.

19. The light irradiation system according to claim 16, wherein in the light irradiation device,
a protruding portion configured to be inserted into the through-hole of the catheter is provided on a distal end side of the large diameter portion.

20. The light irradiation system according to claim 14, wherein the inner diameter of the catheter is equal to the outer diameter of the large diameter portion of the light irradiation device.

* * * * *